US009339035B2

(12) United States Patent
Slomczynska et al.

(10) Patent No.: US 9,339,035 B2
(45) Date of Patent: May 17, 2016

(54) COMPOSITIONS AND METHODS FOR CONTROLLING NEMATODE PESTS

(75) Inventors: Urszula Slomczynska, Ballwin, MO (US); Matt W. Dimmic, Maryland Heights, MO (US); William P. Haakenson, Jr., St. Louis, MO (US); Al Wideman, St. Louis, MO (US); Michael J. Crawford, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 349 days.

(21) Appl. No.: 13/819,880

(22) PCT Filed: Aug. 31, 2011

(86) PCT No.: PCT/US2011/049847
§ 371 (c)(1),
(2), (4) Date: Jul. 18, 2013

(87) PCT Pub. No.: WO2012/030887
PCT Pub. Date: Mar. 8, 2012

(65) Prior Publication Data
US 2013/0303368 A1 Nov. 14, 2013

Related U.S. Application Data

(60) Provisional application No. 61/379,514, filed on Sep. 2, 2010.

(51) Int. Cl.
| A01N 43/64 | (2006.01) |
| C07D 409/04 | (2006.01) |
| C07D 405/04 | (2006.01) |
| A01N 43/713 | (2006.01) |
| C07D 257/06 | (2006.01) |
| C07D 403/04 | (2006.01) |
| A01C 1/06 | (2006.01) |

(52) U.S. Cl.
CPC . *A01N 43/64* (2013.01); *A01C 1/06* (2013.01); *A01N 43/713* (2013.01); *C07D 257/06* (2013.01); *C07D 403/04* (2013.01); *C07D 405/04* (2013.01); *C07D 409/04* (2013.01)

(58) Field of Classification Search
CPC ... A01N 43/64; A01N 43/713; C07D 257/06; C07D 403/04; C07D 405/04; C07D 409/04
USPC .................. 504/100, 116.1; 514/382; 548/252
See application file for complete search history.

(56) References Cited

U.S. PATENT DOCUMENTS

| 3,509,153 | A | * | 4/1970 | Wallace et al. ............... 544/366 |
| 4,465,017 | A | | 8/1984 | Simmons |
| 4,759,945 | A | | 7/1988 | Nemecek et al. |
| 4,791,124 | A | | 12/1988 | Lutomski et al. |
| 4,908,357 | A | | 3/1990 | Lutomski |
| 5,080,925 | A | | 1/1992 | Kouno |
| 5,107,787 | A | | 4/1992 | Kouno |
| 5,389,399 | A | | 2/1995 | Bazin et al. |
| 5,393,767 | A | | 2/1995 | Dick |
| 5,554,445 | A | | 9/1996 | Struszczyk et al. |
| 5,891,246 | A | | 4/1999 | Lund |
| 5,918,413 | A | | 7/1999 | Otani et al. |
| 6,048,714 | A | | 4/2000 | Hiromoto |
| 6,310,049 | B1 | | 10/2001 | Wada et al. |
| 8,017,555 | B2 | | 9/2011 | Slomczynska et al. |
| 8,410,023 | B2 | | 4/2013 | Slomczynska et al. |
| 2002/0013326 | A1 | | 1/2002 | Tiebes et al. |
| 2003/0162812 | A1 | | 8/2003 | Harmsen et al. |
| 2004/0186295 | A1 | | 9/2004 | Cosford et al. |
| 2004/0209776 | A1 | | 10/2004 | Farooq et al. |
| 2004/0220199 | A1 | | 11/2004 | Asrar et al. |
| 2007/0135506 | A1 | | 6/2007 | Zeun et al. |
| 2009/0048311 | A1 | | 2/2009 | Williams et al. |
| 2010/0267714 | A1 | | 10/2010 | Jorgensen et al. |
| 2013/0067620 | A1 | | 3/2013 | Bradley et al. |

FOREIGN PATENT DOCUMENTS

| DE | 19923317 A1 | 11/2000 |
| EP | 0339854 B1 | 5/1993 |
| WO | 8706429 A1 | 11/1987 |
| WO | 02076983 A1 | 10/2002 |
| WO | 02100826 A2 | 12/2002 |
| WO | 03018008 A1 | 3/2003 |
| WO | 03029210 A2 | 4/2003 |
| WO | 2004110351 A2 | 12/2004 |
| WO | 2006097030 A1 | 9/2006 |
| WO | 2007039782 A1 | 4/2007 |
| WO | 2007103456 A2 | 9/2007 |
| WO | 2007130820 A2 | 11/2007 |

(Continued)

OTHER PUBLICATIONS

Atkins, J.M. and Vedejs, E., A two-stage iterative process for the synthesis of poly-oxazoles, Organic Letters, 2005, vol. 7, No. 15, p. 3351-3354.
Shkumat, A.P. et al, 2-(2-furyl)- and 2-(2-thienyl)-5aryloxazoles, Ukrainskii Khimicheskii Zhurnal, 1987, 53/5:529-533, XP-002728980, CAPLUS RECORD 1988:75262, 1 page.
CAS Registry No. 678167-41-4; STN Entry Date Apr. 30, 2004, 2-(2-chlorophenyl)-5-(2-methyl-3-furanyl)-1,3,4-Oxadiazole.
Cesarini, S., et al., "1,3,4-Oxadiazole Formation as Traceless Release in Solid Phase Organic Synthesis," 2006, Tetrahedron, 62/43:10223-10236.
Klyuchnikova, O.A., et al., "Some Reactions of Tetrazolylthiopheses," 2005, Izvestiya Vysshikh Uchebnykh Zavedenii, Khimiya i Khimicheskaya Tekhnologiya, 48/10:53-58 (English abstract only).
Machida et al., "Photochemistry of the nitrogen-thiocarbonyl systems. Part 1. Photoinduced reactions. Part 68. Photocycloaddition of arylcarbothioamides with unsaturated systems. Synthesis of 3,5-diaryl-1,2,4-thiadiazoles and 3-aryl-4,4,5,5-tramethylisothiazolines via photogenerated nitrile sulfides," 1984, Tetrahedron Ltrs, 25/4:409-10, CAPLUS, Document No. 100:174747, 2 pages.
Obukhov, A.E., "Localization of the pump-induced electron interaction and of spin-orbital coupling or the near-lying singlet and triplet excited states in the impurity generation of light in the series multiatomic molecules," 2004, Proceedings of SPIE-The International Society for Optical Engineering, 5402:400-411.

(Continued)

Primary Examiner — Janet Epps-Smith
Assistant Examiner — Courtney Brown
(74) Attorney, Agent, or Firm — Senniger Powers LLP; Molly B. Edwards

(57) ABSTRACT

Compositions and processes for controlling nematodes are described herein, e.g., nematodes that infest plants or animals. The compounds include certain 2,5-substituted tetrazoles.

21 Claims, No Drawings

(56) References Cited

FOREIGN PATENT DOCUMENTS

| WO | 2007130822 A2 | 11/2007 |
|---|---|---|
| WO | WO 2007130820 A2 * | 11/2007 |
| WO | 2007149395 A2 | 12/2007 |
| WO | 2008049864 A1 | 5/2008 |
| WO | 2009023721 A1 | 2/2009 |
| WO | 2010093650 A2 | 8/2010 |

OTHER PUBLICATIONS

Patsenker et al., "Acylation of 5-phenyl-2-(fur-2-yl)oxazole," 1997, Chem Hetero Compounds, 33/11:1277-1271, XP055136874.

Pulici et al., "Trifluoroacetic Anhydride-Mediated Soled-Phase Version of the Robinson-Gabriel Synthesis of Oxazoles," 2005, J Combinatorial Chem, 7/3:463-473, XP055136879.

Shang, Z., "Oxidative cyclization of aromatic aldehyde N-acylhydrazones by bis(trifluroacetoxy)iodobenzene", Synthetic Communications, 2006, 36(20), 2927-2937.

Sung, H-H., et al., Novel Alternating Fluorene-based Conjugated Polymers Containing Oxadiazole Pendants with Various Terminal Groups, 2004, Macromolecules, 37/21:7945-7954.

Zhang, Z., et al., "Studies on the synthesis and biological activity of 2-aryl-5-(5-methylisoxazole-3-yl)-1, 3, 4-oxadiazole derivatives and related property", Lanzhou Daxue Xuebao, ZiranKexueban, 1992, 28(2), 103-111 (English Abstract only).

Yan et al., "Organic reactions in ionic liquids. Oxidative dimerisation of thioamides with phenyliodine(III) diacetate," 2003, J Chem Res, 10:618-619, CAPLUS, Doc No. 1400.357270.

Ito et al., "A Medium-Term Rat Liver Bioassay for Rapid in vivo Detection of Carcinogenic Potential of Chemicals," 2003, Cancer Science, 94:3-8.

Ito, S., et al., "a Facile Synthesis of 2,5-Disubstituted Tetrazoles by the Reaction of Phenylsulfonylhydrazones with Arenediazonium Salts," 1976, Bull Chem Soc JP, 49(7):1920-1923.

Kang, S.Y., et al., "Tetrazole-Biarylpyrazole Derivatives as Cannabinoid CB1 receptor Antagonists," 2008, Bioorg & Medic Chem Ltrs, 18:2385-2389.

Mishra et al., "Basics and Potential Applications of Surfactants—A Review," 2009, Int'l J of Pharm Tech Res, 1 (4):1354-1365.

Nelson, D.W., et al., "Structure-Activity Relationship Studies on a Series of Novel, Substituted 1-Benzyl-5-Phenyltetrazole P2X67 Antagonists," 2006, J Med Chem, 49:3659-3666.

Wagner, G., et al., "Hit-to-Lead Optimization of Disubstituted Oxadiazoles and Tetrazoles as mGluR5 NAMS," 2010, Bioorg & Medic Chem Ltrs, 20:3737-3741.

CAPLUS, Latif et al., "Carbonyl and Thiocarbonyl Compounds. Part XVII. Newer Polyhalo-1,3-benzodioxoles and carbamates incorporating Methylenedioxphenyl Structure," 1980, Indian J of Chem, Section B: Organic Chemistry including Medicinal Chemistry, 19B, 975-979.

Weaver, G.W., "Product Class 8: 1,3,4-Oxadiazoles," 2004, Science of Synthesis, 13:219-251, 35 pages.

Latif, N., et al., "Carbonyl & Thiocarbonyl Compounds: Part XVII-Newer Polyhalo-I,3-benzodioxoles & Carbamates Incorporating Methylenedioxyphenyl Structure," 1980, India J Chem, 19B/11:975-979.

Barker, K.R., et al. "Plant and Soil Nematodes: Societal Impact and Focus for the Future," 1994, J Nematology, 26/2:127-137.

Becker, H., "Seeking New Controls for Costly Nematodes," 1999, Agricultural Research Magazine, 47(3):22-24.

Carpenter, J., et al., "Township Limits on 1,3-D Will Impact Adjustment to Methyl Bromide Phase-Out," 2001, California Agriculture, 55(3):12-18.

Carter, C., "Costs Uncertain: Methyl Bromide Phase-Out Becomes Reality," 2001, California Agriculture, 55(3):2.

Crow, W.T., "Alternatives to Fenamiphos for Management of Plant-Parasitic Nematodes on Bermudagrass," 2005, Journal of Nematology, 37/4/:477-482.

Davydov, D.V., et al., "Regioselective Arlyation of N-Tributylstannylated 5-Substituted Tetrazoles by Diaryliodonium Salts in the Presence of Cu(OAc)2," 2002, Tetrahedron Letters, Elsevier, Amsterdam, NL, 43/35:6217-6219, XP027241945.

Duval, R., et al., "Rapid Discovery of Triazolobenzylidene-Thiazolopyrimidines (TBTP) as CDC25 Phosphatase Inhibitors by Parallel Click Chemistry and in Situ Screening" 2009, J Combin Chem, 11:947-950.

Enders, C., et al., "End-Group Telechelic Oligo- and Polythiophenes by "Click" Reactions: Synthesis and Analysis via LC-ESI-TOF MS," 2010, Macromolecules, 43:8436-8446.

Fiandanese, V., et al., "A Straightforward Synthesis of Benzofuran- and Indole-Substituted 1,2,3-Triazoles via Click Chemistry," 2009, Synthesis, 22:3853-3859.

Flynn, B.L., et al., "Discovery of 7-Hydroxy-6-methoxy-2-methyl-3-(3,4,5-trimethoxybenzoyl)benzo[b]furan (BNC105), a Tubulin Polymerization Inhibitor with Potent Antiproliferative and Tumor Vascular Disrupting Properties," 2011, J Med Chem, 54:6014-6027.

Geerts, S., et al., "Anthelmintic Resistance in Human Helminths: Learning From the Problems with Worm Control in Livestock," 1997, Parasitology Today 13:149-151.

Guven, O.O., "Synthesis and characterization of some novel 4-furyl substituted 3-imidazoline 3-oxides," 2007, General Papers, ARKIVOC, (XV), 142-147.

Hackney, R.W., et al., "Marigold, Castor Bean, and Chrysanthemum as Controls of Meliodogyne Incognita and Pratylenchus alleni," 1975, J Nematol 7(1):84-90.

Hwang, E., et al., "Semiconducting polymer thin films by surface-confined stepwise click polymerization," 2011, Chem Comm, 47:11990, Supp Info (2), 15 pages.

Hwang, E., et al., "Semiconducting polymer thin films by surface-confined stepwise click polymerization," 2011, Chem Comm, 47:11990-11992.

Kinzel, T., et al., "A New Palladium Precatalyst Allows for the Fast Suzuki-Miyaura Coupling Reactions of Unstable Polyfluorophenyl and 2-Heteroaryl Boronic Acids," 2010, JACS, 132:14073-14075.

Kumar,D., et al. "An Efficient, One-Pot, Regioselective Synthesis of 1,4-Diaryl-1H-1,2,3-triazoles Using Click Chemistry," 2010, SYNTHESIS, 10:1687-1691.

Nia, A.S., et al., "Hydrogen-bonded perylene/terthiophene-materials: synthesis and spectroscopic properties," 2012, TETRAHEDRON, 68:722-729.

Potratz, S., et al., "Thiophene-based Donor—Acceptor Co-Oligomers by Copper-Catalyzed 1,3-Dipolar Cycloaddition," 2012, Beilstein JOC, 8:683-692.

Prichard, R., "Anthelmintic Resistance," 1994, Veterinary Parasitology, 54:259-268.

Sangster, N.C., et al., "Pharmacology of Anthelmintic Resistance," 1999, Parasitology Today 15(4):141-146.

Schillinger, E-K., et al., "Oligothiophene Versus b-Sheet Peptide: Synthesis and Self-Assembly of an Organic Semiconductor-Peptide Hybrid," 2009, Adv Materials, 21/I16:1562-1567.

Shawali, A.S., et al., "Azo Coupling of Benzenesulfonylhydrazones of Heterocyclic Aldehydes," 1979, J Heterocyclic Chem, 16/1:123-128, Wiley-Blackwell Publishing, Inc., XP002623113.

Shaytan, A.K., et al., "Self-Assembling Nanofibers from Thiophene Peptide Diblock Oligomers: A Combined Experimental and Computer Simulations Study," 2011, ACS NANO, 5/9:6894-6909.

Smith, N.D., et al., "Discovery of Highly Potent, Selective, Orally Bioavailable, Metabotropic Glutamate Subtype 5 (mGlu5) Receptor Antagonists Devoid of Cytochrome P450 1A2 Inhibitory Activity," 2004, Biorganic & Medicinal Chemistry Letters, 14/22:5481-5484, Pergamon, Elsevier Science, GB, XP004598578.

Andersen, J., et al., "Rapid Synthesis of Aryl Azides from Aryl Halides Under Mild Conditions," 2005, Synlett, 14:2209-2213.

Lörincz et al., "The Sequential Sonogashira-Click Reaction: A Versatile 4-Aryl-1,2,3-triazoles," 2009, Synthesis, 20:3527-3532.

* cited by examiner

COMPOSITIONS AND METHODS FOR CONTROLLING NEMATODE PESTS

BACKGROUND

Nematodes (derived from the Greek word for thread) are active, flexible, elongate, organisms that live on moist surfaces or in liquid environments, including films of water within soil and moist tissues within other organisms. While only 20,000 species of nematode have been identified, it is estimated that 40,000 to 10 million actually exist. Many species of nematodes have evolved to be very successful parasites of plants and animals and are responsible for significant economic losses in agriculture and livestock and for morbidity and mortality in humans (Whitehead (1998) *Plant Nematode Control*. CAB International, New York).

Nematode parasites of plants can infest all parts of plants, including roots, developing flower buds, leaves, and stems. Plant parasites are classified on the basis of their feeding habits into the broad categories migratory ectoparasites, migratory endoparasites, and sedentary endoparasites. Sedentary endoparasites, which include the root knot nematodes (*Meloidogyne*) and cyst nematodes (*Globodera* and *Heterodera*) induce feeding sites and establish long-term infections within roots that are often very damaging to crops (Whitehead, supra). It is estimated that parasitic nematodes cost the horticulture and agriculture industries in excess of $78 billion worldwide a year, based on an estimated average 12% annual loss spread across all major crops. For example, it is estimated that nematodes cause soybean losses of approximately $3.2 billion annually worldwide (Barker et al. (1994) *Plant and Soil Nematodes: Societal Impact and Focus for the Future*. The Committee on National Needs and Priorities in Nematology. Cooperative State Research Service, US Department of Agriculture and Society of Nematologists). Several factors make the need for safe and effective nematode controls urgent. Continuing population growth, famines, and environmental degradation have heightened concern for the sustainability of agriculture, and new government regulations may prevent or severely restrict the use of many available agricultural anthelmintic agents.

There are a very small array of chemicals available to effectively control nematodes (Becker (1999) *Agricultural Research Magazine* 47(3):22-24; U.S. Pat. No. 6,048,714). In general, chemical nematicides are highly toxic compounds known to cause substantial environmental damage and are increasingly restricted in the amounts and locations in which they can be used. For example, the soil fumigant methyl bromide which has been used effectively to reduce nematode infestations in a variety of specialty crops, is regulated under the U.N. Montreal Protocol as an ozone-depleting substance and is undergoing phase out in the US and world wide (Carter (2001) *California Agriculture*, 55(3):2). It is expected that strawberry and other commodity crop industries will be significantly impacted if a suitable replacement for methyl bromide is not found. Similarly, broad-spectrum nematicides such as Telone (various formulations of 1,3-dichloropropene) have significant restrictions on their use because of toxicological concerns (Carter (2001) *California Agriculture*, 55(3):12-18). Organophosphate and carbamate pesticides are another important class of nematicides undergoing regulatory review and several of these compounds are currently being phase out (e.g., fenamiphos, terbufos, cadusafos).

To date little success has been achieved in finding safe effective replacements for the toxic but efficacious conventional nematicides. A recent example of the poor efficacy of many newer potential replacements for organophosphates and carbamates is the study of alternatives to fenamiphos for management of plant parasitic nematodes in bermudagrass. In these trials, none of the experimental treatments reduced population densities of the plant parasitic nematodes, or consistently promoted turf visual performance or turf root production (Crow (2005) *Journal of Nematology*, 37(4):477-482). Consequently there remains an urgent need to develop environmentally safe, efficacious methods of controlling plant parasitic nematodes Some plant species are known to be highly resistant to nematodes. The best documented of these include marigolds (*Tagetes* spp.), rattlebox (*Crotalaria spectabilis*), chrysanthemums (*Chrysanthemum* spp.), castor bean (*Ricinus communis*), margosa (*Azardiracta indica*), and many members of the family Asteraceae (family Compositae) (Hackney & Dickerson. (1975) *J Nematol* 7(1):84-90). In the case of the Asteraceae, the photodynamic compound alpha-terthienyl has been shown to account for the strong nematicidal activity of the roots. Castor beans are plowed under as a green manure before a seed crop is set. However, a significant drawback of the castor plant is that the seed contains toxic compounds (such as ricin) that can kill humans, pets, and livestock and is also highly allergenic. In most cases however, the active principle(s) for plant nematicidal activity has not been discovered and it remains difficult to derive commercially successful nematicidal products from these resistant plants or to transfer the resistance to crops of agronomical importance such as soybeans and cotton.

Genetic resistance to certain nematodes is available in some commercial cultivars (e.g., soybeans), but these are restricted in number and the availability of cultivars with both desirable agronomic features and resistance is limited. Furthermore, the production of nematode resistant commercial varieties by conventional plant breeding based on genetic recombination through sexual crosses is a slow process and is often further hampered by a lack of appropriate germplasm.

Chemical means of controlling plant parasitic nematodes continue to be essential for many crops which lack adequate natural resistance or a source of transgenic resistance. In the specialty markets, economic hardship resulting from nematode infestation is particularly high in strawberries, bananas, and other high value vegetables and fruits. In the high-acreage crop markets, nematode damage is greatest in soybeans and cotton. There are however, dozens of additional crops that suffer from significant nematode infestation including potato, pepper, onion, citrus, coffee, sugarcane, greenhouse ornamentals and golf course turf grasses.

To be useful in modern agriculture nematicides must have high potency, a broad spectrum of activity against different strains of nematodes and should not be toxic to non-target organisms.

Nematode parasites of vertebrates (e.g., humans, livestock and companion animals) include gut roundworms, hookworms, pinworms, whipworms, and filarial worms. They can be transmitted in a variety of ways, including by water contamination, skin penetration, biting insects, or by ingestion of contaminated food.

In domesticated animals, nematode control or "de-worming" is essential to the economic viability of livestock producers and is a necessary part of veterinary care of companion animals. Parasitic nematodes cause mortality in animals (e.g., heartworm in dogs and cats) and morbidity as a result of the parasites' inhibiting the ability of the infected animal to absorb nutrients. The parasite-induced nutrient deficiency leads to disease and stunted growth in livestock and companion animals. For instance, in cattle and dairy herds, a single untreated infection with the brown stomach worm can permanently restrict an animal's ability to convert feed into muscle mass or milk.

Two factors contribute to the need for novel anthelmintics and vaccines to control animal parasitic nematodes. First, some of the more prevalent species of parasitic nematodes of livestock are building resistance to the anthelmintic drugs available currently, meaning that these products are losing their efficacy. These developments are not surprising because few effective anthelmintic drugs are available and most have been used continuously. Some parasitic species have developed resistance to most of the anthelmintics (Geents et al. (1997) *Parasitology Today* 13:149-151; Prichard (1994) *Veterinary Parasitology* 54:259-268). The fact that many of the anthelmintic drugs have similar modes of action complicates matters, as the loss of sensitivity of the parasite to one drug is often accompanied by side resistance—that is, resistance to other drugs in the same class (Sangster & Gill (1999) *Parasitology Today* 15(4):141-146). Secondly, there are some issues with toxicity for the major compounds currently available.

Infections by parasitic nematode worms also result in substantial human mortality and morbidity, especially in tropical regions of Africa, Asia, and the Americas. The World Health Organization estimates 2.9 billion people are infected, and in some areas, 85% of the population carries worms. While mortality is rare in proportion to infections, morbidity is substantial and rivals diabetes and lung cancer in worldwide disability adjusted life year (DALY) measurements.

Examples of human parasitic nematodes include hookworms, filarial worms, and pinworms. Hookworms (1.3 billion infections) are the major cause of anemia in millions of children, resulting in growth retardation and impaired cognitive development. Filarial worms invade the lymphatics, resulting in permanently swollen and deformed limbs (elephantiasis), and the eyes, causing African river blindness. The large gut roundworm *Ascaris lumbricoides* infects more than one billion people worldwide and causes malnutrition and obstructive bowel disease. In developed countries, pinworms are common and often transmitted through children in daycare.

Even in asymptomatic parasitic infections, nematodes can still deprive the host of valuable nutrients and increase the ability of other organisms to establish secondary infections. In some cases, infections can cause debilitating illnesses and can result in anemia, diarrhea, dehydration, loss of appetite, or death.

Despite some advances in drug availability and public health infrastructure and the near elimination of one tropical nematode (the water-borne Guinea worm), most nematode diseases have remained intractable problems. Treatment of hookworm diseases with anthelmintic drugs, for instance, has not provided adequate control in regions of high incidence because rapid re-infection occurs after treatment. In fact, over the last 50 years, while nematode infection rates have fallen in the United States, Europe, and Japan, the overall number of infections worldwide has kept pace with the growing world population. Large scale initiatives by regional governments, the World Health Organization, foundations, and pharmaceutical companies are now underway attempting to control nematode infections with currently available tools, including three programs for control of Onchocerciasis (river blindness) in Africa and the Americas using ivermectin and vector control; The Global Alliance to Eliminate Lymphatic Filariasis using DEC, albendazole, and ivermectin; and the highly successful Guinea Worm Eradication Program. Until safe and effective vaccines are discovered to prevent parasitic nematode infections, anthelmintic drugs will continue to be used to control and treat nematode parasitic infections in both humans and domestic animals.

Certain insecticidal oxazoles (U.S. Pat. No. 4,791,124) and thiazoles (U.S. Pat. No. 4,908,357) and nematicidal pyrazoles (U.S. Pat. No. 6,310,049) have been disclosed in the art. The present invention discloses specific tetrazole compounds with surprisingly potent nematicidal activity showing activity comparable to commercial standards. Commercial level nematicidal potency has not previously been demonstrated with tetrazoles. Importantly, these compounds are broadly active against nematodes yet safe to non-target organisms.

SUMMARY

Compositions and methods for controlling nematodes, e.g., nematodes that infest plants or the situs of plants, are described herein. Nematodes that parasitize a vertebrate (e.g., a human or a non-human vertebrate, particularly one subject to or infected by a one or more species of nematode) can also be controlled using the methods and compositions described herein.

Described herein are nematicidal compositions comprising an effective amount of a compound or a mixture of compounds having any of the formula described herein, for example the compounds shown below.

Described herein is a compound of Formula I or a salt, e.g., a pharmaceutically acceptable salt, thereof,

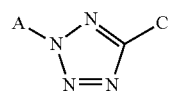

Formula I wherein,

A is an optionally substituted aryl or optionally substituted arylalkyl (e.g., arylC1alkyl or arylC2alkyl) or optionally substituted aryloxo or optionally substituted arylthio, or optionally substituted heteroaryl (including pyridyl, pyrazyl, oxazolyl or isoxazolyl) or optionally substituted heteroarylalkyl (e.g., heteroarylC1alkyl or heteroarylC2alkyl or heteroarylC3alkyl or heteroarylC4alkyl) or optionally substituted heteroaryloxo or optionally substituted heteroarylthio wherein said substituents are selected from the group consisting of halo, C1-C6 haloalkyl, C6-C10 aryl, C4-C7 cycloalkyl, C2-C6 alkyl, C2-C6 alkenyl, C2-C6 alkynyl, C6-C10 aryl (C1-C6)alkyl, C6-C10 aryl(C2-C6)alkenyl, C6-C10 aryl(C2-C6)alkynyl, C1-C6 hydroxyalkyl, amino, ureido, cyano, C1-C6 acylamino, hydroxy, thiol, C1-C6 acyloxy, azido, C1-C6 alkoxy and carboxy, C(H)O;

and

C is a heteroaryl (including thienyl, furanyl, oxazolyl and isoxazolyl) each of which can be optionally independently substituted with one or more substituents selected from: fluorine, chlorine, CH$_3$ and OCF$_3$ or an optionally independently substituted pyrrolidinyl (including pyrrolidinyl-1, pyrrolidinyl-2 and pyrrolidinyl-3) or optionally independently substituted piperidinyl (including piperidinyl-1, piperidinyl-2 or piperidinyl-3 and piperidinyl-4) or an optionally independently substituted pyrrolyl (including pyrrolyl-1, pyrrolyl-2 or pyrrolyl-3) or optionally independently substituted pyrroyloxo (including pyrrolyl-2 and pyrrolyl-3) or optionally independently substituted pyrrolythio (including pyrrolyl-2 and pyrrolyl-3) or optionally independently substituted pyrrolylalkyl (e.g., pyrrolyl C1 alkyl and pyrrolyl C2 alkyl) (including pyrrolyl-1, pyrrolyl-2 and pyrrolyl-3) wherein the substituents are selected from the group consisting of methyl, alkyl (e.g., C2, C3, C4, C5 and C6 alkyl), cycyl, heterocycl, hydroxyalkyl and halogen.

A compound of Formula Ia or a salt thereof,

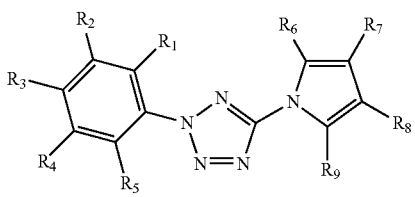

Formula Ia wherein,
R$_1$ and R$_5$ are independently selected from hydrogen, CH$_3$, F, Cl, Br, CF$_3$ and OCF$_3$;
R$_2$ and R$_4$ are independently selected from hydrogen, F, Cl, Br, and CF$_3$;
R$_3$ is selected from hydrogen, CH$_3$, CF$_3$, F, Cl, Br, OCF$_3$, OCH$_3$, CN, and C(H)O
R$_6$, R$_7$, R$_8$ and R$_9$ are independently selected from hydrogen, CH$_3$, alkyl, cykloalkyl, heterocyl, and halogen.

A compound of Formula Ib or a salt thereof,

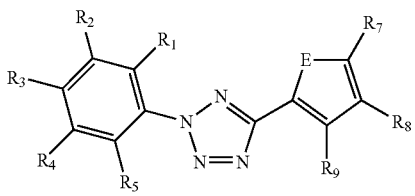

Formula Ib wherein,
R$_1$ and R$_5$ are independently selected from hydrogen, CH$_3$, F, Cl, Br, CF$_3$, OCF$_3$
R$_2$ and R$_4$ are independently selected from hydrogen, F, Cl, Br, CF$_3$:
R$_3$ is selected from hydrogen, CH$_3$, CF$_3$, F, Cl, Br, OCF$_3$, OCH$_3$, CN, C(H)O;
R$_7$, R$_8$ and R$_9$ are independently selected from hydrogen, F, Cl, Br, CH$_3$, OCF$_3$;
E is O or S.

A compound of Formula Ic or a salt thereof,

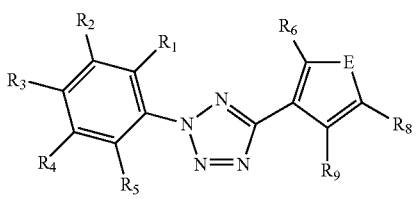

Formula Ic wherein,
R$_1$ and R$_5$ are independently selected from hydrogen, CH$_3$, F, Cl, Br, CF$_3$, OCF$_3$;
R$_2$ and R$_4$ are independently selected from hydrogen, F, Cl, Br, CF$_3$;
R$_3$ is selected from hydrogen, CH$_3$, CF$_3$, F, Cl, Br, OCF$_3$, OCH$_3$, CN, C(H)O;

R$_6$, R$_8$ and R$_9$ are independently selected from hydrogen, F, Cl, Br, CH$_3$, OCF$_3$;
E is O or S.

A compound of Formula Id or a salt thereof,

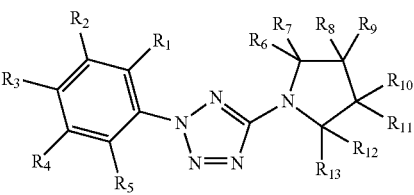

Formula Id wherein,
R$_1$ and R$_5$ are independently selected from hydrogen, CH$_3$, F, Cl, Br, CF$_3$ and OCF$_3$;
R$_2$ and R$_4$ are independently selected from hydrogen, F, Cl, Br, and CF$_3$;
R$_3$ is selected from hydrogen, CH$_3$, CF$_3$, F, Cl, Br, OCF$_3$, OCH$_3$, CN, and C(H)O;
R$_6$ through R$_{13}$ are independently selected from hydrogen, CH$_3$, alkyl, cykloalkyl, heterocyl, and halogen:

A compound of Formula II or a salt, e.g., a pharmaceutically acceptable salt, thereof,

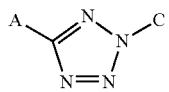

Formula II wherein,
A is an optionally independently substituted aryl or optionally independently substituted arylalkyl (e.g., arylC1alkyl and arylC2alkyl) or optionally independently substituted aryloxo or optionally independently substituted arylthio, or optionally independently substituted heteroaryl (including pyridyl, pyrazyl, oxazolyl and isoxazolyl) or optionally independently substituted heteroarylalkyl (e.g., heteroarylC1alkyl or heteroarylC2alkyl or heteroarylC3alkyl or heteroarylC4alkyl) or optionally independently substituted heteroaryloxo or optionally independently substituted heteroarylthio wherein said substituents are selected from the group consisting of halo, methyl, C1-C6 haloalkyl, C6-C10 aryl, C4-C7 cycloalkyl, C2-C6 alkyl, C2-C6 alkenyl, C2-C6 alkynyl, C6-C10 aryl(C1-C6)alkyl, C6-C10 aryl(C2-C6)alkenyl, C6-C10 aryl(C2-C6)alkynyl, C1-C6 hydroxyalkyl, amino, ureido, cyano, C1-C6 acylamino, hydroxy, thiol, C1-C6 acyloxy, azido, C1-C6 alkoxy and carboxy, C(H)O; and;

C is a heteroaryl including thienyl, furanyl, oxazolyl or isoxazolyl each of which can be optionally independently substituted with one or more substituents selected from: fluorine, chlorine, CH$_3$ and OCF$_3$ or an optionally independently substituted pyrrolidinyl (including pyrrolidinyl-1, pyrrolidinyl-2 and pyrrolidinyl-3) or optionally independently substituted piperidinyl (including piperidinyl-1, piperidinyl-2 or piperidinyl-3 and piperidinyl-4) or an optionally independently substituted pyrrolyl (including pyrrolyl-1, pyrrolyl-2 and pyrrolyl-3) or optionally independently substituted pyrrolyloxo (including pyrrolyl-2 and pyrrolyl-3) or optionally independently substituted pyrrolythio (including pyrrolyl-2 and pyrrolyl-3) or optionally independently substituted independently pyrrolylalkyl (e.g., pyrrolyl C1 alkyl and pyrrolyl C2 alkyl) (including pyrrolyl-1, pyrrolyl-2 and pyrrolyl-3) wherein the substituents are selected from the group consisting of methyl, alkyl (e.g., C2, C3, C4, C5 and C6 alkyl), cycyl, heterocycl, hydroxyalkyl and halogen.

A compound of Formula IIa or a salt thereof,

Formula IIa wherein,
- $R_1$ and $R_5$ are independently selected from hydrogen, $CH_3$, F, Cl, Br, $CF_3$ and $OCF_3$;
- $R_2$ and $R_4$ are independently selected from hydrogen, F, Cl, Br, and $CF_3$;
- $R_3$ is selected from hydrogen, $CH_3$, $CF_3$, F, Cl, Br, $OCF_3$, $OCH_3$, CN, and C(H)O;
- $R_6$; $R_7$, $R_8$ and $R_9$ are independently selected from hydrogen, $CH_3$, alkyl, cykloalkyl, heterocyl, and halogen.

A compound of Formula IIb or a salt thereof,

Formula IIb wherein,
- $R_1$ and $R_5$ are independently selected from hydrogen, $CH_3$, F, Cl, Br, $CF_3$, $OCF_3$
- $R_2$ and $R_4$ are independently selected from hydrogen, F, Cl, Br, $CF_3$:
- $R_3$ is selected from hydrogen, $CH_3$, $CF_3$, F, Cl, Br, $OCF_3$, $OCH_3$, CN, C(H)O;
- $R_7$, $R_8$ and $R_9$ are independently selected from hydrogen, F, Cl, Br, $CH_3$, $OCF_3$;
- E is O or S.

A compound of Formula IIc or a salt thereof,

Formula IIc wherein,
- $R_1$ and $R_5$ are independently selected from hydrogen, $CH_3$, F, Cl, Br, $CF_3$, $OCF_3$;
- $R_2$ and $R_4$ are independently selected from hydrogen, F, Cl, Br, $CF_3$;
- $R_3$ is selected from hydrogen, $CH_3$, $CF_3$, F, Cl, Br, $OCF_3$, $OCH_3$, CN, C(H)O;

- $R_6$, $R_8$ and $R_9$ are independently selected from hydrogen, F, Cl, Br, $CH_3$, $OCF_3$;
- E is O or S.

A compound of Formula IId or a salt thereof,

Formula IId wherein,
- $R_1$ and $R_5$ are independently selected from hydrogen, $CH_3$, F, Cl, Br, $CF_3$ and $OCF_3$;
- $R_2$ and $R_4$ are independently selected from hydrogen, F, Cl, Br, and $CF_3$;
- $R_3$ is selected from hydrogen, $CH_3$, $CF_3$, F, Cl, Br, $OCF_3$, $OCH_3$, CN, and C(H)O;
- $R_6$ through $R_{13}$ are independently selected from hydrogen, $CH_3$, alkyl, cykloalkyl, heterocyl, and halogen:

Also described herein is a method for control of unwanted nematodes, the method comprising administering to mammals, birds, or their food, plants, seeds or soil a composition comprising an effective amount of a compound of any of Formulas I, Ia, Ib, Ic, Id, II, IIa, IIb, IIc and IId.

In some cases the method entails controlling plant parasitic nematodes and comprises administering to plant subject to attack by (or already infected by) such nematodes, the seeds of such plants or the soil in which such plants are grown or are to be planted.

Also described is a nematicidal composition comprising a compound of any of Formulas I, Ia, Ib, Ic, Id, II, IIa, IIb, IIc and IId at a concentration sufficient to reduce the viability of a parasitic nematode.

In some cases, the nematicidal composition further includes an aqueous surfactant. Examples of surfactants that can be used include, Span 20, Span 40, Span 80, Span 85, Tween 20, Tween 40, Tween 80, Tween 85, Triton X 100, Makon 10, Igepal CO 630, Brij 35, Brij 97, Brij 58, Brij 78, Brij 98, Tergitol TMN 6, Dowfax 3B2, Physan, Agrimer VA6 and Toximul TA 15. In some cases, the nematicidal composition further includes a permeation enhancer (e.g., cyclodextrin). In some cases, the nematicidal composition further includes a co-solvent. Examples of co-solvents that can be used include ethyl lactate, methyl soyate/ethyl lactate co-solvent blends (e.g., Steposol), isopropanol, acetone, 1,2-propanediol, n-alkylpyrrolidones (e.g., the Agsolex series), a petroleum based-oil (e.g., aromatic 200) or a mineral oil (e.g., paraffin oil)). In some cases, the nematicidal composition further includes another pesticide (e.g., nematicide, insecticide or fungicide) such as an avermectin (e.g., abamectin, ivermectin), milbemycin, fluensulfone, chlothianidin, thiamethoxam, imidacloprid, thiodicarb, aldicarb, oxamyl, fenamiphos, fosthiazate, metam sodium, etridiazole, pentachloro-nitrobenzene (PCNB), flutolanil, metalaxyl, mefonoxam, and fosetyl-al. Useful fungicides include, but are not limited to, silthiofam, fludioxonil, myclobutanil, azoxystrobin, trifloxystrobin, chlorothalonil, propiconazole, tebuconazole and pyraclostrobin. The composition may also comprise herbicides (e.g., trifloxysulfuron, glyphosate, halosulfuron) and other chemicals for disease control (e.g., chitosan).

Also described is a nematicidal composition comprising: tetrazole analogs or mixtures of analogs selected from the group consisting of the compounds 2-phenyl-5-(thiophen-2-yl)-2H-tetrazole, 5-(furan-2-yl)-2-phenyl-2H-tetrazole, 2-(4-chlorophenyl)-5-(thiophen-2-yl)-2H-tetrazole, 2-(4-chlorophenyl)-5-(furan-2-yl)-2H-tetrazole, 2-(4-chloro-2-methylphenyl)-5-(thiophen-2-yl)-2H-tetrazole, 2-(4-chloro-2-methylphenyl)-5-(furan-2-yl)-2H-tetrazole, 5-phenyl-2-(thiophen-2-yl)-2H-tetrazole, 2-(furan-2-yl)-5-phenyl-2H-tetrazole, 5-(4-chlorophenyl)-2-(thiophen-2-yl)-2H-tetrazole, 5-(4-chlorophenyl)-2-(furan-2-yl)-2H-tetrazole, 5-(4-chloro-2-methylphenyl)-2-(thiophen-2-yl)-2H-tetrazole, 5-(4-chloro-2-methylphenyl)-2-(furan-2-yl)-2H-tetrazole.

In various embodiments the composition further comprises an aqueous surfactant. Examples of surfactants that can be used include, Span 20, Span 40, Span 80, Span 85, Tween 20, Tween 40, Tween 80, Tween 85, Triton X 100, Makon 10, Igepal CO 630, Brij 35, Brij 97, Brij 58, Brij 78, Brij 98, Tergitol TMN 6, Dowfax 3B2, Physan, Agrimer VA6 and Toximul TA 15. In some cases, the nematicidal composition further includes a permeation enhancer (e.g., cyclodextrin). In some cases, the nematicidal composition further includes a co-solvent. Examples of co-solvents that can be used include ethyl lactate, methyl soyate/ethyl lactate co-solvent blends (e.g., Steposol), isopropanol, acetone, 1,2-propanediol, n-alkylpyrrolidones (e.g., the Agsolex series), a petroleum based-oil (e.g., aromatic 200) or a mineral oil (e.g., paraffin oil)). In some cases, the nematicidal composition further includes another pesticide (e.g., nematicide, insecticide or fungicide) such as an avermectin (e.g., abamectin, ivermectin), milbemycin, fluensulfone, clothianidin, thiamethoxam, imidacloprid, thiodicarb, aldicarb, oxamyl, fenamiphos, fosthiazate, metam sodium, etridiazole, penta-chloro-nitrobenzene (PCNB), flutolanil, metalaxyl, mefonoxam, and fosetyl-al. Useful fungicides include, but are not limited to, silthiofam, fludioxonil, myclobutanil, azoxystrobin, trifloxystrobin, chlorothalonil, propiconazole, tebuconazole and pyraclostrobin. The composition may also comprise herbicides (e.g., trifloxysulfuron, glyphosate, halosulfuron) and other chemicals for disease control (e.g., chitosan).

Also described is a method for control of unwanted parasitic nematode (e.g., nematodes other than *C. elegans*), the method including administering to vertebrates, plants, seeds or soil a nematicidal composition including a compound of any of the formulae described herein in any of the nematicidal compositions described herein.

In some instances, the nematode infects plants and the nematicidal composition is applied to the soil or to plants. In some instances, the nematicidal composition is applied to soil before planting. In some instances, the nematicidal composition is applied to soil after planting. In some instances, the nematicidal composition is applied to soil using a drip system. In some instances, the nematicidal composition is applied to soil using a drench system. In some instances, the nematicidal composition is applied to plant roots or plant foliage (e.g., leaves, stems). In some instances the nematicide composition is tilled into the soil or applied in furrow. In some instances, the nematicidal composition is applied to seeds. In some instances, the nematode parasite infects a vertebrate. In some instances the nematicidal composition is administered to a vertabrate (e.g., a human or a non-human vertabrate, particularly one subject to or infected by a one or more species of nematode). In some instances, the nematicidal composition is administered to non-human vertebrate. In some instances, the nematicidal composition is administered to a human. In some instances, the nematicidal composition is formulated as a drench to be administered to a non-human animal. In some instances, the nematicidal composition is formulated as an orally administered drug. In some instances, the nematicidal composition is formulated as an injectable drug. In some instances, the nematicidal composition is formulated for topical applications such as pour-ons, or for the use in tags or collars.

Also described herein is a method of treating a disorder (e.g., an infection) caused by a parasitic nematode, (e.g., *M. incognita, H. glycines, B. longicaudatus, H. contortus, A. suum, B. malayi*) in a subject, e.g., a host plant, animal, or person. The method includes administering to the subject an effective amount of a compound having formula I, Ia, Ib, Ic, Id, II, IIa, IIb, IIc or IId. The compound may be delivered by several means including pre-planting, post-planting, seed treatment and as a feed additive, drench, external application, pill or by injection.

In still another aspect, methods of inhibiting a parasitic nematode (e.g., *M. incognita, H. glycines, B. longicaudatus, H. contortus, A. suum, B. malayi*) are provided. Such methods can include contacting the nematode (at any stage of growth), with a compound, e.g., a compound having Formula I, Ia, Ib, Ic, Id, II, IIa, IIb, IIc or IId is provided.

In another aspect, methods of reducing the viability or fecundity or slowing the growth or development or inhibiting the infectivity of a nematode using a nematicidal compound, e.g., a compound having Formula I, Ia, Ib, Ic, Id, II, IIa, IIb, IIc or IId is provided. Such methods can include contacting the nematode with specific a compound, e.g., a compound having Formula I, Ia, Ib, Ic, Id, II, IIa, IIb, IIc or IId; (c) reducing the viability or fecundity of the nematode parasite.

Also described is a method for reducing the viability, growth, or fecundity of a nematode parasite, the method comprising exposing the nematode to a compound having Formula I, Ia, Ib, Ic, Id, II, IIa, IIb, IIc or IId and a method of protecting a plant from a nematode infection, the method comprising applying to the plant, to the soil, or to seeds of the plant an compound a compound having Formula I, Ia, Ib, Ic, Id, II, IIa, IIb, IIc or IId.

Also described is a method for protecting a vertebrate (e.g., a bird or a mammal) from a nematode infection, the method comprising administering to the vertebrate a compound having Formula I, Ia, Ib, Ic, Id, II, IIa, IIb, IIc or IId. The bird can be a domesticated fowl (e.g., a chicken, turkey, duck, or goose). The mammal can be a domesticated animal, e.g., a companion animal (e.g., a cat, dog, horse or rabbit) or livestock (e.g., a cow, sheep, pig, goat, alpaca or llama) or can be a human.

Described herein are methods for controlling nematodes parasites by administering a compound described herein. The methods include administering to vertebrates, plants, seeds or soil a nematicidal composition comprising:

(a) an effective amount of a compound or a mixture of compounds having any of the formulae described herein, for example one of the following formulas:

Formulas:

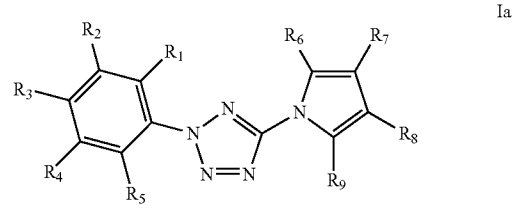

Ia

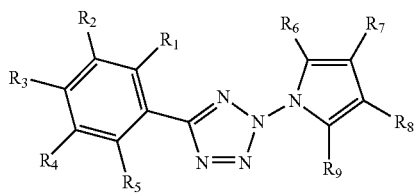

IIa wherein,
- $R_1$ and $R_5$ are independently selected from hydrogen, $CH_3$, F, Cl, Br, $CF_3$ and $OCF_3$;
- $R_2$ and $R_4$ are independently selected from hydrogen, F, Cl, Br, and $CF_3$;
- $R_3$ is selected from hydrogen, $CH_3$, $CF_3$, F, Cl, Br, $OCF_3$, $OCH_3$, CN, and CO;
- $R_6$, $R_7$, $R_8$ and $R_9$ are independently selected from hydrogen, $CH_3$, alkyl, cykloalkyl, heterocyl, and halogen:

Formulas:

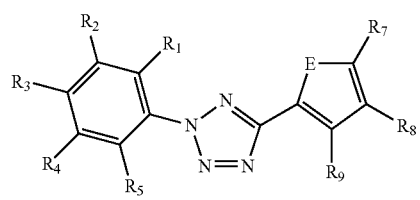

Ib

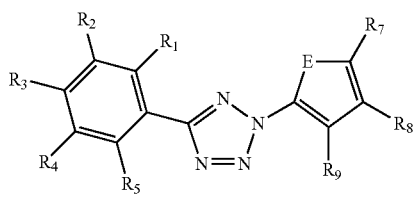

IIb wherein,
- $R_1$ and $R_5$ are independently selected from hydrogen, $CH_3$, F, Cl, Br, $CF_3$, $OCF_3$
- $R_2$ and $R_4$ are independently selected from hydrogen, F, Cl, Br, $CF_3$:
- $R_3$ is selected from hydrogen, $CH_3$, $CF_3$, F, Cl, Br, $OCF_3$, $OCH_3$, CN, C(H)O;
- $R_7$, $R_8$ and $R_9$ are independently selected from hydrogen, F, Cl, Br, $CH_3$, $OCF_3$;
- E is O or S;

Formulas:

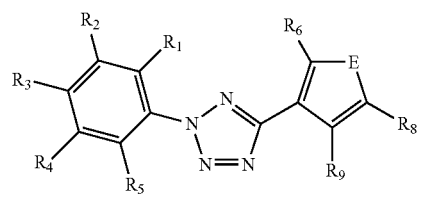

Ic

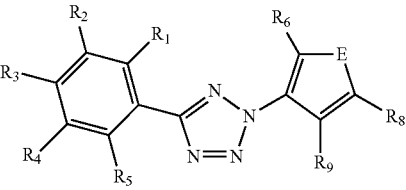

IIc wherein,
- $R_1$ and $R_5$ are independently selected from hydrogen, $CH_3$, F, Cl, Br, $CF_3$, $OCF_3$;
- $R_2$ and $R_4$ are independently selected from hydrogen, F, Cl, Br, $CF_3$;
- $R_3$ is selected from hydrogen, $CH_3$, $CF_3$, F, Cl, Br, $OCF_3$, $OCH_3$, CN, C(H)O;
- $R_6$, $R_8$ and $R_9$ are independently selected from hydrogen, F, Cl, Br, $CH_3$, $OCF_3$;
- E is O or S;

Formulas:

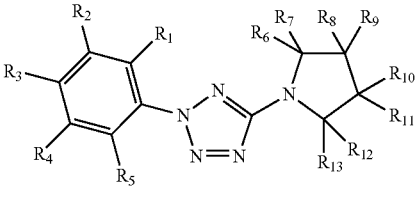

Id

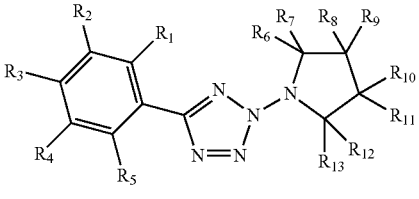

IId wherein,
- $R_1$ and $R_5$ are independently selected from hydrogen, $CH_3$, F, Cl, Br, $CF_3$ and $OCF_3$;
- $R_2$ and $R_4$ are independently selected from hydrogen, F, Cl, Br, and $CF_3$;
- $R_3$ is selected from hydrogen, $CH_3$, $CF_3$, F, Cl, Br, $OCF_3$, $OCH_3$, CN, and C(H)O;
- $R_6$ through $R_{13}$ are independently selected from hydrogen, $CH_3$, alkyl, cykloalkyl, heterocyl, and halogen:

The compositions can also include an aqueous surfactant. Examples of surfactants that can be used include, Span 20, Span 40, Span 80, Span 85, Tween 20, Tween 40, Tween 80, Tween 85, Triton X 100, Makon 10, Igepal CO 630, Brij 35, Brij 97, Brij 58, Brij 78, Brij 98, Tergitol TMN 6, Dowfax 3B2, Physan, Agrimer VA6 and Toximul TA 15. In some cases, the nematicidal composition further includes a permeation enhancer (e.g., cyclodextrin). In some cases, the nematicidal composition further includes a co-solvent. Examples of co-solvents that can be used include ethyl lactate, methyl soyate/ethyl lactate co-solvent blends (e.g., Steposol), isopropanol, acetone, 1,2-propanediol, n-alkylpyrrolidones (e.g., the Agsolex series), a petroleum based-oil (e.g., aromatic 200) or a mineral oil (e.g., paraffin oil)). In some cases, the nematicidal composition further includes another pesticide (e.g., nematicide, insecticide or fungicide) such as an avermectin (e.g., abamectin, ivermectin), milbemycin, fluensulfone, chlothianidin, thiamethoxam, imidacloprid, thiodicarb, aldicarb, oxamyl, fenamiphos, fosthiazate, metam sodium, etridiazole, penta-chloro-nitrobenzene (PCNB), flutolanil, metalaxyl, mefonoxam, and fosetyl-al. Useful fungicides include, but are not limited to, silthiofam, fludioxonil, myclobutanil, azoxystrobin, trifloxystrobin, chlorothalonil, propiconazole, tebuconazole and pyraclostrobin. The composition may also comprise herbicides (e.g., trifloxysulfuron, glyphosate, halosulfuron) and other chemicals for disease control (e.g., chitosan).

Also featured is a method for control of unwanted nematodes comprising administering to plants, seeds or soil a nematicidal composition comprising an effective amount of: (a) a compound selected from the group consisting of 2-phenyl-5-(thiophen-2-yl)-2H-tetrazole, 5-(furan-2-yl)-2-phenyl-2H-tetrazole, 2-(4-chlorophenyl)-5-(thiophen-2-yl)-2H-tetrazole, 2-(4-chlorophenyl)-5-(furan-2-yl)-2H-tetrazole, 2-(4-chloro-2-methylphenyl)-5-(thiophen-2-yl)-2H-tetrazole, 2-(4-chloro-2-methylphenyl)-5-(furan-2-yl)-2H-tetrazole, 5-phenyl-2-(thiophen-2-yl)-2H-tetrazole, 2-(furan-2-yl)-5-phenyl-2H-tetrazole, 5-(4-chlorophenyl)-2-(thiophen-2-yl)-2H-tetrazole, 5-(4-chlorophenyl)-2-(furan-2-yl)-2H-tetrazole, 5-(4-chloro-2-methylphenyl)-2-(thiophen-2-yl)-2H-tetrazole, 5-(4-chloro-2-methylphenyl)-2-(furan-2-yl)-2H-tetrazole.

Also featured is a method for control of unwanted nematodes comprising administering to vertebrates (e.g., a human or a non-human vertabrate, particularly one subject to or infected by a one or more species of nematode) a nematicidal composition comprising an effective amount of: (a) a compound selected from the group consisting of 2-phenyl-5-(thiophen-2-yl)-2H-tetrazole, 5-(furan-2-yl)-2-phenyl-2H-tetrazole, 2-(4-chlorophenyl)-5-(thiophen-2-yl)-2H-tetrazole, 2-(4-chlorophenyl)-5-(furan-2-yl)-2H-tetrazole, 2-(4-chloro-2-methylphenyl)-5-(thiophen-2-yl)-2H-tetrazole, 2-(4-chloro-2-methylphenyl)-5-(furan-2-yl)-2H-tetrazole, 5-phenyl-2-(thiophen-2-yl)-2H-tetrazole, 2-(furan-2-yl)-5-phenyl-2H-tetrazole, 5-(4-chlorophenyl)-2-(thiophen-2-yl)-2H-tetrazole, 5-(4-chlorophenyl)-2-(furan-2-yl)-2H-tetrazole, 5-(4-chloro-2-methylphenyl)-2-(thiophen-2-yl)-2H-tetrazole, 5-(4-chloro-2-methylphenyl)-2-(furan-2-yl)-2H-tetrazole.

In certain embodiments of the method the composition further comprises an aqueous surfactant. Examples of surfactants that can be used include, Span 20, Span 40, Span 80, Span 85, Tween 20, Tween 40, Tween 80, Tween 85, Triton X 100, Makon 10, Igepal CO 630, Brij 35, Brij 97, Brij 58, Brij 78, Brij 98, Tergitol TMN 6, Dowfax 3B2, Physan, Agrimer VA6 and Toximul TA 15. In some cases, the nematicidal composition further includes a permeation enhancer (e.g., cyclodextrin). In some cases, the nematicidal composition further includes a co-solvent. Examples of co-solvents that can be used include ethyl lactate, methyl soyate/ethyl lactate co-solvent blends (e.g., Steposol), isopropanol, acetone, 1,2-propanediol, n-alkylpyrrolidones (e.g., the Agsolex series), a petroleum based-oil (e.g., aromatic 200) or a mineral oil (e.g., paraffin oil)). In some cases, the nematicidal composition further includes another pesticide (e.g., nematicide, insecticide or fungicide) such as an avermectin (e.g., abamectin, ivermectin), milbemycin, fluensulfone, chlothianidin, thiamethoxam, imidacloprid, thiodicarb, aldicarb, oxamyl, fenamiphos, fosthiazate, metam sodium, etridiazole, penta-chloro-nitrobenzene (PCNB), flutolanil, metalaxyl, mefonoxam, and fosetyl-al. Useful fungicides include, but are not limited to, silthiofam, fludioxonil, myclobutanil, azoxystrobin, trifloxystrobin, chlorothalonil, propiconazole, tebuconazole and pyraclostrobin. The composition may also comprise herbicides (e.g., trifloxysulfuron, glyphosate, halosulfuron) and other chemicals for disease control (e.g., chitosan); the nematode infects plants and the nematicidal composition is applied to the soil or to plants; the nematicidal composition is applied to soil before planting; the nematicidal composition is applied to soil after planting; the nematicidal composition is applied to soil using a drip system; the nematicidal composition is applied to soil using a drench system; the nematicidal composition is applied to plant roots; the pesticidal composition is applied to seeds; the nematicidal composition is applied to the foliage of plants; the nematode infects a vertebrate; the nematicidal composition is administered to a bird or non-human mammal; the nematicidal composition is administered to a human; the nematicidal composition is formulated as a drench to be administered to a non-human animal; the nematicidal composition is formulated as an orally administered drug; and the nematicidal composition is formulated as an injectable drug.

The methods described hereon are particularly valuable for the control nematodes attacking the roots of desired crop plants, ornamental plants, and turf grasses. The desired crop plants can be, for example, soybeans, cotton, corn, tobacco, wheat, strawberries, tomatoes, banana, sugar cane, sugar beet, potatoes, or citrus.

Also described is a nematicidal feed for a non-human vertebrate including:
(a) a feed; and
(b) a nematicidal composition, including a nematicidal composition described herein.

In some instances, the feed is selected from the group consisting of: soy, wheat, corn, sorghum, millet, alfalfa, clover, and rye.

Also described are feeds that have been supplemented to include one or more of the compounds described herein.

A nematicidal feed for a non-human vertebrate can comprise: (a) an animal feed; and (b) an effective amount of a nematicidal compound or mixtures of compounds having any of the formulae described herein, for example having one of the formula below:

Formulas:

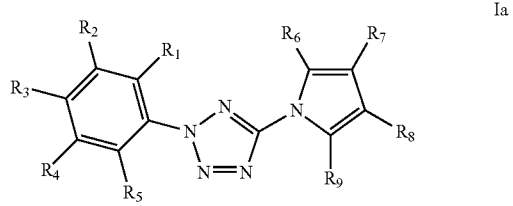

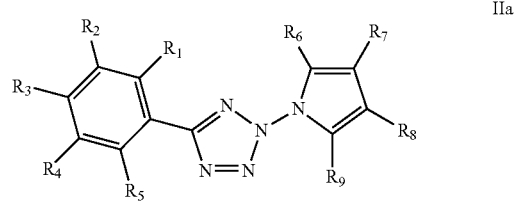

wherein,
$R_1$ and $R_5$ are independently selected from hydrogen, $CH_3$, F, Cl, Br, $CF_3$ and $OCF_3$;
$R_2$ and $R_4$ are independently selected from hydrogen, F, Cl, Br, and $CF_3$;

$R_3$ is selected from hydrogen, $CH_3$, $CF_3$, F, Cl, Br, $OCF_3$, $OCH_3$, CN, and C(H)O;

$R_6$, $R_7$, $R_8$ and $R_9$ are independently selected from hydrogen, $CH_3$, alkyl, cykloalkyl, heterocyl, and halogen:

Formulas:

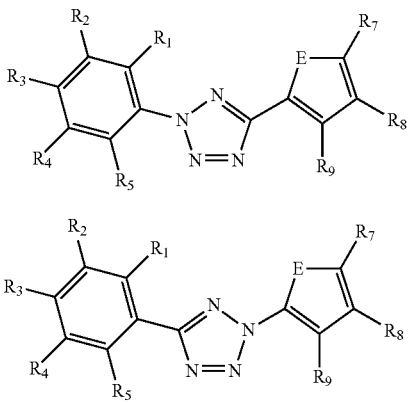

Ib

IIb wherein,
$R_1$ and $R_5$ are independently selected from hydrogen, $CH_3$, F, Cl, Br, $CF_3$, $OCF_3$
$R_2$ and $R_4$ are independently selected from hydrogen, F, Cl, Br, $CF_3$:
$R_3$ is selected from hydrogen, $CH_3$, $CF_3$, F, Cl, Br, $OCF_3$, $OCH_3$, CN, C(H)O;
$R_7$, $R_8$ and $R_9$ are independently selected from hydrogen, F, Cl, Br, $CH_3$, $OCF_3$;
E is O or S;

Formulas:

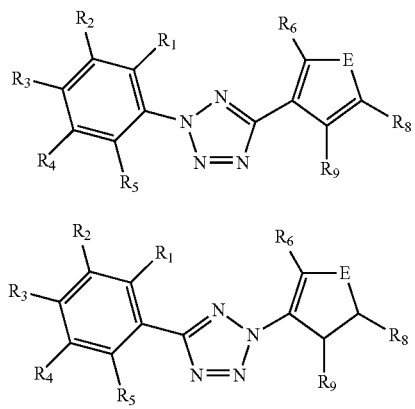

Ic

IIc wherein,
$R_1$ and $R_5$ are independently selected from hydrogen, $CH_3$, F, Cl, Br, $CF_3$, $OCF_3$;
$R_2$ and $R_4$ are independently selected from hydrogen, F, Cl, Br, $CF_3$;
$R_3$ is selected from hydrogen, $CH_3$, $CF_3$, F, Cl, Br, $OCF_3$, $OCH_3$, CN, C(H)O;
$R_6$, $R_8$ and $R_9$ are independently selected from hydrogen, F, Cl, Br, $CH_3$, $OCF_3$;
E is O or S;

Formulas:

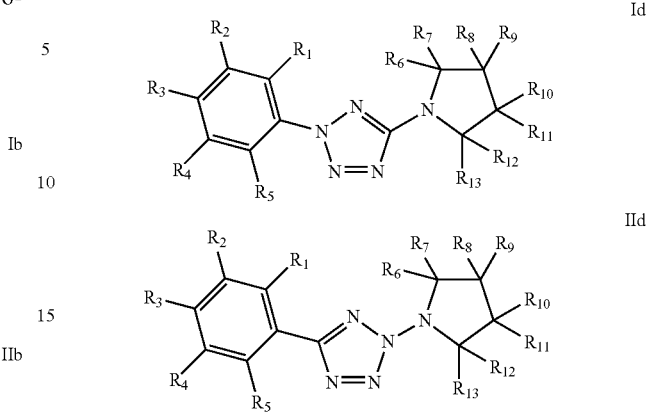

Id

IId wherein,
$R_1$ and $R_5$ are independently selected from hydrogen, $CH_3$, F, Cl, Br, $CF_3$ and $OCF_3$;
$R_2$ and $R_4$ are independently selected from hydrogen, F, Cl, Br, and $CF_3$;
$R_3$ is selected from hydrogen, $CH_3$, $CF_3$, F, Cl, Br, $OCF_3$, $OCH_3$, CN, and C(H)O;
$R_6$ through $R_{13}$ are independently selected from hydrogen, $CH_3$, alkyl, cykloalkyl, heterocyl, and halogen:

The feed can be selected from the group consisting of: soy, wheat, corn, sorghum, millet, alfalfa, clover, and rye.

As used herein, an agent with "anthelmintic or anthelminthic or antihelminthic activity" is an agent, which when tested, has measurable nematode-killing activity or results in reduced fertility or sterility in the nematodes such that fewer viable or no offspring result, or compromises the ability of the nematode to infect or reproduce in its host, or interferes with the growth or development of a nematode. The agent may also or instead display nematode repellant properties. In the assay, the agent is combined with nematodes, e.g., in a well of microtiter dish, in liquid or solid media or in the soil containing the agent. Staged nematodes are placed on the media. The time of survival, viability of offspring, and/or the movement of the nematodes are measured. An agent with "anthelmintic or anthelminthic or antihelmthic activity" can, for example, reduce the survival time of adult nematodes relative to unexposed similarly staged adults, e.g., by about 20%, 40%, 60%, 80%, or more. In the alternative, an agent with "anthelmintic or anthelminthic or antihelminthic activity" may also cause the nematodes to cease replicating, regenerating, and/or producing viable progeny, e.g., by about 20%, 40%, 60%, 80%, or more. The effect may be apparent immediately or in successive generations.

The term "halo" or "halogen" refers to any radical of fluorine, chlorine, bromine or iodine.

The term "alkyl" as employed herein by itself or as part of another group refers to both straight and branched chain radicals of up to ten carbons. Typical C1-10 (a reference to, for example, C1-C6 alkyl includes C1, C2, C3, C4, C5, C6, C2-C4, C3-C6, etc.)alkyl groups include methyl, ethyl, propyl, isopropyl, butyl, sec-butyl, tert-butyl, 3-pentyl, hexyl and octyl groups, which may be optionally substituted.

The term "alkenyl" as employed herein by itself or as part of another group means a straight or branched chain radical of 2-10 carbon atoms, unless the chain length is otherwise specified, including at least one double bond between two of the carbon atoms in the chain. Typical alkenyl groups include ethenyl, 1-propenyl, 2-propenyl, 2-methyl-1-propenyl, 1-butenyl and 2-butenyl.

The term "alkynyl" is used herein to mean a straight or branched chain radical of 2-10 carbon atoms, unless the chain length is limited thereto, wherein there is at least one triple bond between two of the carbon atoms in the chain. Typical alkynyl groups include ethynyl, 1-propynyl, 1-methyl-2-propynyl, 2-propynyl, 1-butynyl and 2-butynyl.

Alkoxy (e.g., methoxy and ethoxy) groups contain oxygen substituted by one of the C1-10 alkyl groups mentioned above, which may be optionally substituted.

Alkylthio groups contain sulfur substituted by one of the C1-10 alkyl groups mentioned above, which may be optionally substituted. Also included are the sulfoxides and sulfones of such alkylthio groups.

Amino groups include —$NH_2$, —$NHR_{15}$ and —$NR_{15}R_{16}$, wherein $R_{15}$ and $R_{16}$ are C1-10 alkyl or cycloalkyl groups, or $R_{15}$ and $R_{16}$ are combined with the N to form a ring structure, such as a piperidine, or $R_{15}$ and $R_{16}$ are combined with the N and other group to form a ring, such as a piperazine. The alkyl group may be optionally substituted.

The term "aryl" as employed herein by itself or as part of another group refers to monocyclic, bicyclic or tricyclic aromatic groups containing from 6 to 14 (e.g., 6 or 8) carbons in the ring.

Common aryl groups include C6-14 aryl, preferably C6-10 aryl. Typical C6-14 aryl groups include phenyl, naphthyl, phenanthrenyl, anthracenyl, indenyl, azulenyl, biphenyl, biphenylenyl and fluorenyl groups.

Cycloalkyl groups are C3-8 cycloalkyl. Typical cycloalkyl groups include cyclopropyl, cyclobutyl, cyclopentyl, cyclohexyl and cycloheptyl.

The term "arylalkyl" is used herein to mean any of the above-mentioned C1-10 alkyl groups substituted by any of the above-mentioned C6-14 aryl groups. Preferably the arylalkyl group is benzyl, phenethyl or naphthylmethyl. Preferred arylalkyl groups are arylC1alkyl and arylC2alkyl.

The term "arylalkenyl" is used herein to mean any of the above-mentioned C2-10 alkenyl groups substituted by any of the above-mentioned C6-14 aryl groups.

The term "arylalkynyl" is used herein to mean any of the above-mentioned C2-10 alkynyl groups substituted by any of the above-mentioned C6-14 aryl groups.

The term "aryloxy" is used herein to mean oxygen substituted by one of the above-mentioned C6-14 aryl groups, which may be optionally substituted. Common aryloxy groups include phenoxy and 4-methylphenoxy.

The term "arylalkoxy" is used herein to mean any of the above mentioned C1-10 alkoxy groups substituted by any of the above-mentioned aryl groups, which may be optionally substituted. Example arylalkoxy groups include benzyloxy and phenethyloxy.

Example haloalkyl groups include C1-10 alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Acylamino (acylamido) groups include any C1-6 acyl (alkanoyl) attached to an amino nitrogen, e.g., acetamido, chloroacetamido, propionamido, butanoylamido, pentanoylamido and hexanoylamido, as well as aryl-substituted C1-6 acylamino groups, e.g., benzoylamido, and pentafluorobenzoylamido.

Common acyloxy groups are any C1-6 acyl (alkanoyl) attached to an oxy (—O—) group, e.g., formyloxy, acetoxy, propionoyloxy, butanoyloxy, pentanoyloxy and hexanoyloxy.

The term heterocycle is used herein to mean a saturated or partially saturated 3-7 membered monocyclic, or 7-10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable.

Common saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

The term "heteroaryl" as employed herein refers to groups having 5 to 14 ring atoms; 6, 10 or 14π electrons shared in a cyclic array; and containing carbon atoms and 1, 2 or 3 oxygen, nitrogen or sulfur heteroatoms.

Example heteroaryl groups include thienyl (thiophenyl), benzo[b]thienyl, naphtho[2,3-b]thienyl, thianthrenyl, furyl (furanyl), pyranyl, isobenzofuranyl, chromenyl, xanthenyl, phenoxanthiinyl, pyrrolyl, including without limitation 2H-pyrrolyl, imidazolyl, pyrazolyl, pyridyl(pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-α]pyrimidin-4-one, pyrazolo[1,5-α]pyrimidinyl, including without limitation pyrazolo[1,5-α]pyrimidin-3-yl, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

The term "heteroaryloxy" is used herein to mean oxygen substituted by one of the above-mentioned heteroaryl groups, which may be optionally substituted. Useful heteroaryloxy groups include pyridyloxy, pyrazinyloxy, pyrrolyloxy, pyrazolyloxy, imidazolyloxy and thiophenyloxy.

The term "heteroarylalkoxy" is used herein to mean any of the above-mentioned C1-10 alkoxy groups substituted by any of the above-mentioned heteroaryl groups, which may be optionally substituted.

A preferred pyrrolalkyl is pyrrol C1 alkyl.

Preferred furanlalkyl, thienylalkyl, oxazolyalkyl and isoxazolylalkyl groups are furanlC1alkyl, thienylC1alkyl, oxazolyC1alkyl and isoxazolylC1alkyl respectively.

A permeation enhancer is generally an agent that facilitates the active compounds of the invention.

A co-solvent (i.e., a latent solvent or indirect solvent) is an agent that becomes an effective solvent in the presence of an active solvent and can improve the properties of the primary (active) solvent.

The composition can be produced in concentrated form that includes little or no water. The composition can be diluted with water or some other solvent prior to use to treat plants, seeds, soil or vertebrates.

The details of one or more embodiments of the invention are set forth in the accompanying drawings and the description below. Other features, objects, and advantages of the invention will be apparent from the description and drawings, and from the claims.

DETAILED DESCRIPTION

Described herein are certain tetrazole compounds with potent broad spectrum nematicidal activity.

The nematicidal compounds may be supplied to plants exogenously, through sprays for example. These compounds may also be applied as a seed coat. The compounds can be applied to plants or the environment of plants needing nematode control, or to animals or the food of animals needing nematode parasite control. The compositions may be applied by, for example drench or drip techniques. With drip applications compounds can be applied directly to the base of the plants or the soil immediately adjacent to the plants. The composition may be applied through existing drip irrigation systems. This procedure is particularly applicable for cotton, strawberries, tomatoes, potatoes, vegetables and ornamental plants. Alternatively, a drench application can be used where a sufficient quantity of nematicidal composition is applied such that it drains to the root area of the plants. The drench technique can be used for a variety of crops and turf grasses. The drench technique can also be used for animals. Preferably, the nematicidal compositions would be administered orally to promote activity against internal parasitic nematodes. Nematicidal compositions may also be administered in some cases by injection of the host animal or by topical applications.

The concentration of the nematicidal composition should be sufficient to control the parasite without causing significant phytotoxicity to the desired plant or undue toxicity to the animal host. The compounds disclosed in this invention have a good therapeutic window.

We have surprisingly found that certain tetrazole analogs (e.g., 2-phenyl-5-(thiophen-2-yl)-2H-tetrazole, 5-(furan-2-yl)-2-phenyl-2H-tetrazole, 2-(4-chlorophenyl)-5-(thiophen-2-yl)-2H-tetrazole, 2-(4-chlorophenyl)-5-(furan-2-yl)-2H-tetrazole, 2-(4-chloro-2-methylphenyl)-5-(thiophen-2-yl)-2H-tetrazole, 2-(4-chloro-2-methylphenyl)-5-(furan-2-yl)-2H-tetrazole, 5-phenyl-2-(thiophen-2-yl)-2H-tetrazole, 2-(furan-2-yl)-5-phenyl-2H-tetrazole, 5-(4-chlorophenyl)-2-(thiophen-2-yl)-2H-tetrazole, 5-(4-chlorophenyl)-2-(furan-2-yl)-2H-tetrazole, 5-(4-chloro-2-methylphenyl)-2-(thiophen-2-yl)-2H-tetrazole, 5-(4-chloro-2-methylphenyl)-2-(furan-2-yl)-2H-tetrazole) have nematicidal potencies comparable with organophosphate and carbamate standards yet display excellent selectivity for nematodes over plants and animals. Thus, these analogs will provide useful compounds for nematode parasite control.

The nematicidal agents described herein can be applied in conjunction with another pesticidal agents. The second agent may, for example, be applied simultaneously or sequentially. Such pesticidal agents can include for example, avermectins for animal applications.

The aforementioned nematicidal compositions can be used to treat diseases or infestations caused by nematodes of the following non-limiting, exemplary genera: *Anguina, Ditylenchus, Tylenchorhynchus, Pratylenchus, Radopholus, Hirschmanniella, Nacobbus, Hoplolaimus, Scutellonema, Rotylenchus, Helicotylenchus, Rotylenchulus, Belonolaimus, Heterodera*, other cyst nematodes, *Meloidogyne, Criconemoides, Hemicycliophora, Paratylenchus, Tylenchulus, Aphelenchoides, Bursaphelenchus, Rhadinaphelenchus, Longidorus, Xiphinema, Trichodorus*, and *Paratrichodorus, Dirofiliaria, Onchocerca, Brugia, Acanthocheilonema, Aelurostrongylus, Anchlostoma, Angiostrongylus, Ascaris, Bunostomum, Capillaria, Chabertia, Cooperia, Crenosoma, Dictyocaulus, Dioctophyme, Dipetalonema, Dracunculus, Enterobius, Filaroides, Haemonchus, Lagochilascaris, Loa, Manseonella, Muellerius, Necator, Nematodirus, Oesophagostomum, Ostertagia, Parafilaria, Parascaris, Physaloptera, Protostrongylus, Setaria, Spirocerca, Stephanogilaria, Strongyloides, Strongylus, Thelazia, Toxascaris, Toxocara, Trichinella, Trichostrongylus, Trichuris, Uncinaria*, and *Wuchereria*. Particularly preferred are nematodes including *Dirofilaria, Onchocerca, Brugia, Acanthocheilonema, Dipetalonema, Loa, Mansonella, Parafilaria, Setaria, Stephanofilaria*, and *Wucheria, Pratylenchus, Heterodera, Meloidogyne, Paratylenchus*. Species that are particularly preferred are: *Ancylostoma caninum, Haemonchus contortus, Trichinella spiralis, Trichurs muris, Dirofilaria immitis, Dirofilaria tenuis, Dirofilaria repens, Dirofilari ursi, Ascaris suum, Toxocara canis, Toxocara cati, Strongyloides ratti, Parastrongyloides trichosuri, Heterodera glycines, Heterodera schachtii, Globodera pallida, Globodera rostochiensis, Meloidogyne javanica, Meloidogyne incognita*, and *Meloidogyne arenaria, Radopholus similis, Longidorus elongatus, Meloidogyne hapla, Belonolaimus longicaudatus, Hoplolaimus galeatus, Pratylenchus scribberi, Pratylenchus brachyurus, Pratylenchus zeae* and *Pratylenchus penetrans*.

The following examples are, therefore, to be construed as merely illustrative, and not limitative of the remainder of the disclosure in any way whatsoever. All of the publications cited herein are hereby incorporated by reference in their entirety.

EXAMPLES

Example 1

*M. Incognita* Testing of Several Nematicidal Compounds in a Miniaturized Greenhouse Assay Overview:

The test compound is dissolved in an acetone solution and added to water. A sprouted cucumber seedling is placed into a vial with dry sand and the water-chemical solution is added immediately. Twenty four hours later *Meloidogyne incognita* eggs are added to the vials and 10 to 12 days later the roots are evaluated for nematode galling.

Procedure:

Cucumber seeds are sprouted for 3 days in moist paper towels. Acceptable sprouts should be 3 to 4 cm long with several lateral roots just emerging. Stock solutions of chemistry are prepared in a mixture of acetone and Triton X100 (412 mg in 500 mL) to a final concentration of 5 mg/mL. The chemical stock solution is then added to 10 mL deionized water plus 0.015% Triton X100 and mixed thoroughly. This is enough to test each condition in triplicate. Ten mL dry sand is added to each vial. At this time the solubility of the chemistry is visually determined and recorded as either ppt (large precipitates) or cloudy (fine precipitates). Seedlings are planted by tilting the vial and laying the seedling in the correct orientation so that the cotyledons are just above the sand and then tilting back to cover the radicles with sand. 3.3 ml water/chemical mix is added to each vial and the vials placed in racks under fluorescent light banks. The vials are inoculated two days after planting by adding 500 vermiform *M. incognita* eggs to each vial in 50 uL of deionized or spring water. The vials are then kept under the fluorescent lamps at ambient room temperature and watered as needed with 1 mL deionized water, usually twice during duration of test. Harvest of the cucumber plants is done 10 to 12 days after inoculation by washing sand off the roots. A root gall rating and visual phytotoxicity rating is assigned using the following scales: Gall rating scale (Gall: % root mass galled): 0=0-5%; 1=6-20%; 2=21-50%; and 3=51-100%. The average of the triplicate gall rating is then calculated: green=0.00-0.33 (no galls); yellow=0.67-1.33 (mild galling); orange=1.67-2.33 (moderate galling); red=2.67-3.00 (severe galling). Visual phytotoxicity scale is also assigned (Vis. tox; visual reduction in root mass compared to the control): rs1=mild stunting; rs2=moderate stunting; rs3=severe stunting.

TABLE 1A

Potent nematicidal tetrazole analogs showing examples of substitution compatible with high activity

| Name | Analog | 8/1 ppm gall ratings |
|---|---|---|
| 1 | Cl-phenyl-tetrazole-thiophene | $0^a/0.67^b$ |
| 2 | phenyl-tetrazole-thiophene | $0.33^a/0.67^b$ |
| 3 | Cl,CH3-phenyl-tetrazole-furan | $0^c/1.33^d$ |
| 4 | pyrrolidine-tetrazole-Cl-phenyl | 0.33/1.33 |
| 5 | N-methylpyrrole-tetrazole-phenyl | 0.00/2.33 |
| 6 | phenyl-tetrazole-thiophene (isomer) | 0.00/1.33 |
| 7 | pyrrole-tetrazole-phenyl | 0.33/1.67 |
| Oxamyl (1 ppm) | | $1.33^a, 1.33^b, 0.67^c, 1.67^d$ |

*Data with the same letters are taken from the same test.

A variety of single or double substitutions on the six membered aromatic ring of the phenyl-2-furan and phenyl-2-thiophene tetrazoles are compatible with high nematicidal activity comparable to oxamyl (oxamyl is a highly toxic compounds classified as a toxicity Class I chemical by the US Environmental Protection Agency). Examples of preferred single substitutions include but are not limited to halogens, $CH_3$, $CF_3$, $OCF_3$ and $OCH_3$ especially in the para position (4-position) of the phenyl ring. The phenyl ring can also be multiply substituted in a way compatible with high nematicidal efficacy. Ring numbering system is shown below.

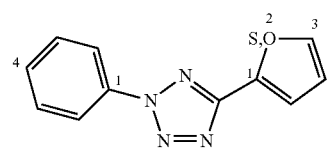

Example 2

General Greenhouse Testing Protocols

Soybean Planting and Growth:

Soybeans seeds are planted in 100% sand in two inch square plastic pots. Chemical treatment is done when the soybeans show the first trifoliate beginning to emerge about 10 to 12 days after planting. At least four hours after chemical application the nematode soybean cyst nematode (SCN) eggs are applied and 28 days after the egg inoculation the test is harvested.

Cucumber Planting and Growth

Cucumber seeds are planted in a sandy soil mixture in two inch square plastic pots. When the cotyledons are fully opened and just as the first leaf begins to emerge, usually 7 days after planting, chemistry for the 7-day treatment is applied. One week later the chemistry for the 0 day treatment is applied. Separate plants are used for each application. The plants are generally in the 1-2 leaf stage now. At least four hours after the chemistry application the pots are inoculated with root knot nematode (RKN) eggs. Plants are rated for galling 14 days after the egg inoculation.

Chemical Formulation and Application

One milligram of chemistry per four pots is equal to one kilogram per hectare of chemical. A standard test uses four replications. For rates above 2 kg/ha, the desired amount of chemical is weighed into a 30 ml vial (example: 8 kg/ha rate=8 mg chemical in 30 ml vial). The chemical is dissolved in 2 ml of appropriate solvent, generally acetone. For rates below 2 kg/ha, 2 milligrams of chemistry is weighed into the vial and dissolved in 2 ml of the solvent. The appropriate amount of chemical concentrate is then pipetted into a separate 30 ml vial and solvent is added to bring the volume to 2 ml (example 0.5 kg/ha=0.5 ml of concentrate+1.5 ml solvent). Each dissolved concentrate is then brought to a total of 20 milliliters using 0.05% Triton X 100 surfactant solution.

Chemical and Nematode Application

Pots to be treated are moist but not saturated. To each of four pots, five milliliters of the appropriate chemical solution is pipetted to the media surface making sure to avoid contact with the base of the plant. Immediately following chemical application, using a mist nozzle, the pot surface is wetted sufficiently to saturate the pot watering in the chemistry. The chemical application is done in the morning.

Nematode eggs, either SCN or RKN, are added to distilled water to create a concentration of 1000 vermiform eggs per liter of water. At least four hours after chemical treatment (0 day testing) or 1 week later (7 day longevity testing) the eggs are applied to the treated pots plus non-treated check plants. A small hole about 1 cm deep is punched into the pot surface. One milliliter of the nematode egg slurry is pipetted into the hole. Immediately afterwards the hole is gently covered. Watering of the test plants is then restricted to only water as needed to prevent wilt for a period of 24 hours. After the 24 hour restricted watering, normal sub-irrigation watering is done for the duration of the test.

TABLE 2A

RKN greenhouse soil assay on cucumber plants

| Name | Analog | 7 day 0.25/ 0.1 kg/ ha rate* |
|---|---|---|
| 1 | [structure: 4-chlorophenyl tetrazole with thiophene] | 92%/89% |
| 2 | [structure: phenyl tetrazole with thiophene] | 53%/47% |
| Fenamiphos | | 94%/80% |

*Data shows percent control (i.e., galling reduction) relative to the control blank treatment. Data with the same letters are taken from the same test.

TABLE 2B

SCN greenhouse soil assay on soybean plants

| Name | Analog | 0 day 0.25 kg/ ha rate* |
|---|---|---|
| 1 | [structure: 4-chlorophenyl tetrazole with thiophene] | 24% |
| 2 | [structure: phenyl tetrazole with thiophene] | 52% |

TABLE 2B-continued

SCN greenhouse soil assay on soybean plants

| Name | Analog | 0 day 0.25 kg/ ha rate* |
|---|---|---|
| 3 | [structure: 3-chloro-2-methylphenyl tetrazole with furan] | 44% |
| Oxamyl | | 75% |
| Fenamiphos | | 90%$^a$ |

*Data shows percent control (i.e., cyst reduction) relative to the control blank treatment. Data with the same letters are taken from the same test.

Certain oxazoles, oxadiazoles and thiadiazoles are highly efficacious nematicides in bioactive soil with potencies comparable to fenamiphos and oxamyl.

Example 3

*Belonalaimus longicaudatus* (Sting Nematode) Testing Protocols

Populations of sting (*Belonolaimus longicaudatus*) nematodes are maintained on St. Augustine turf grass on soil in 15-cm pots. At test initiation the turf is removed from the pots and the soil containing nematode eggs, juveniles, and adults is subdivided into pots each containing a volume of 125 cm$^3$. The compounds to be tested are dissolved in 3 ml of acetone using 3, 6, or 15 mg to achieve equivalent surface area application rates of 2, 4, or 10 kg/ha, respectively. The 3 ml acetone stock solution is added to 30 ml of water, and 5 ml of that solution is used to drench each of 6 replicate test pots prepared as described above. The treated pots containing nematodes are incubated in the laboratory at ambient temperature of approximately 25° C. After 3 days the soil from each pot is washed onto a modified Baermann apparatus comprised of a screen supporting a layer of filter paper on which the soil sample is placed and set in a dish of water. The samples are then incubated at 25° C. for 24 hours to allow the live nematodes to migrate through the paper and screen and into a water reservoir to be collected for counting with a light microscope. Nematodes that have been killed or immobilized by the test compounds are not able to migrate into the reservoir.

Example 4

*C. elegans* and *H. contortus* Testing Protocols

*C. elegans*:

Various compounds were tested for nematicidal activity against *C. elegans* using contact assays in wells. The assays were performed as described below. The test compounds were solubilized in DMSO at 10 mg/ml to create 100× stock solutions. A dilution series was created by diluting the stock solution with DMSO. For each well assay 4 ul of the appropriate dilution is added to a well of a test plate. A 400 ul aliquot of bacterial stock (in M9 buffer with ampicillin) is added to each well of the test plate. Worms are added and the test plate placed on a rotary shaker incubated at 20° C. Worms are examined and scored at 24 hrs, 48 hrs and 72 hours. L1 worms used in the assay are prepared by plating eggs on a plate without a bacterial feeding layer. The eggs hatch and arrest at the L1 stage. This L1 stage population is then used to create a stock for the experiments. A 25 ul aliquot of worms is added to each well in the assay.

*H. contortus:*

The assay was performed essentially as described in: Hubert J, Kerboeuf D. A new method for culture of larvae used in diagnosis of ruminant gastrointestinal strongylosis: comparison with fecal cultures. Can J Comp Med. 1984 48(1):63-71. *H. contortus* eggs were obtained from Myers Parasitology (Magnolia, Ky.). The test compounds were solubilized in DMSO to create 100× stock solutions. 2 ul of compound at various concentrations followed by 200 ul of molten agar were mixed into the wells. Approximately 50 eggs were placed in the well and incubated for 24 hours. After this time, >50% of the eggs were hatched in DMSO controls. After 24 hr, 100 ul of growth medium (Earle's salt solution, 1% yeast extract, 0.9% saline, and sodium bicarbonate to pH 7) containing compound was added to allow larval feeding. After 48 hr in growth medium (total of 72 hours) the wells were evaluated for hatching and larval movement.

TABLE 4A

*C. elegans* well test

| Name | Analog | EC50 ppm 1/2/3 days |
|---|---|---|
| 1 | 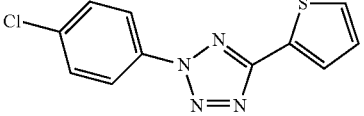 | 0.8/0.8/0.9 |
| 2 | 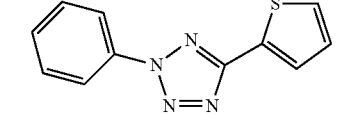 | >50/0.8/0.8 |
| 3 | 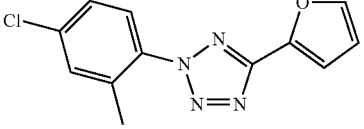 | 0.8/0.8/0.8 |

TABLE 4B

*H. contortus* larval development assay

| Name | Analog | EC50 in ppm at 72 hours |
|---|---|---|
| 1 | 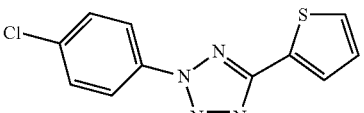 | <6.3 |

TABLE 4B-continued

*H. contortus* larval development assay

| Name | Analog | EC50 in ppm at 72 hours |
|---|---|---|
| 2 | 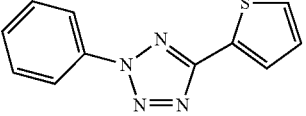 | 6.3-25 |
| 3 | 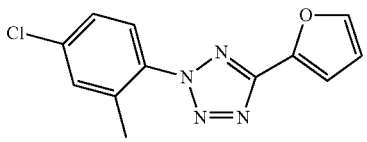 [SMILES: Cc1cc(Cl)ccc1-n1nnc(-c2ccco2)n1] | <6.3 |

These data indicate that the claimed nematicidal tetrazoles have excellent nematode spectrum showing efficacy against clade V nematodes like *C. elegans* and *H. contortus* in addition to clade IVb tylenchid nematodes like *M. incognita* (root knot nematode) and *H. glycines* (soybean cyst nematode).

Example 5

Advanced Greenhouse Testing Protocols

Pre-Plant Incorporated Test (PPI)

The PPI test examines the effect of pre-incorporation of compounds in soil and longer aging to simulate in furrow methods of nematicide application in the field. The PPI test exposes compounds to a higher volume of soil and drying which can result in more severe soil binding. Compounds are also aged for longer periods which can lead to more extensive biotic and abiotic degradation further limiting activity.

The chemically treated soil (sandy soil mix) for all treatment days (e.g., 7 days, 14 days, 21 days) treatments is potted into their appropriate pots. On the same day the 7 day treatment pots are seeded. One week later eggs are applied and 14 days after egg application the test is harvested. The 14 day treatments are planted 7 days after the first planting. The 14 day planting and 7 day inoculation happen on the same day. One week later the 14 day treatments are inoculated with eggs. These are harvested 14 days after the inoculation. The 21 day treatments are planted 14 days after the first planting. The 14 day inoculation and 21 day planting are done on the same day. One week later the 21 day plants are inoculated with eggs. The 7 day treatment is harvested the same day as the 21 day inoculation. Fourteen days after inoculation the 21 day plants are harvested.

| Treatment | Planting | Inoculation | Harvest |
|---|---|---|---|
| 7 day | day 0 | day 7 | day 21 |
| 14 day | day 7 | day 14 | day 28 |
| 21 day | day 14 | day 21 | day 35 |

For each compound a stock is prepared using 4 mg material in 4 ml of acetone. The soil is mixed by placing 80 ml of field soil and 320 ml of sand in a plastic bag and mixing well. The formulation for treatment is done by adding 2.13 ml (8 kg/ha rate), 1.06 ml (4 kg/ha rate) or 0.53 ml (2 kg/ha rate) to a vial and raising it with 10 ml in 0.05%×100. Soil is then treated by adding the entire 10 ml to the 400 ml of mix in the bag. The treated soil is immediately mixed well in the sealed bag to distribute the compound evenly. Approximately 95 ml is used to fill each 2-inch square pot up to the top with some soil compression and flattening. For each compound and for the control treatments 4 pots are filled. All pots are watered until moist but with no run-out through the bottom.

The PPI test simulates 8, 4 and 2 kg/ha rates incorporated 15 cm deep in the field and is equivalent to the 2, 1 and 0.5 kg/ha drench application rates in the standard 2-inch pot cucumber greenhouse assay.

Example 6

Seed Treatment Test of Root Knot Nematode on Cucumber Plants and Soybean Cyst Nematode on Soybean Plants For a given concentration the chemical is dissolved in 500 ul of acetone and one gram of cucumber seed (RKN test) or soybean seed (SCN test) is added (e.g., 20 mg active ingredient in 500 ul acetone plus 1 gram of seed). The seed solutions are agitated until all seeds were thoroughly covered with the chemical solution. The acetone is then allowed to evaporate by air drying the seeds. The seeds are planted in 3-inch (RKN) or 4-inch (SCN) pots containing sandy soil and then the pots are inoculated with 1000 *Meloidogyne incognita* (RKN) or 1000 *Heterodera glycines* (SCN) eggs per pot three days after planting. Plants are rated for galling 14 days after egg inoculation for RKN or 28 days after egg inoculation for SCN.

Example 7

Description of Synthesis of the Compounds of the Formulas I to IId

The compounds of this invention of the Formulas I to IId may be prepared using methods known to those skilled in the art. Specifically, the compounds of this invention with Formula Ia can be prepared as illustrated by the exemplary reaction in Scheme 1.

The compounds of this invention of the Formulas I to IId may be prepared using methods known to those skilled in the art. Specifically, the compounds of this invention with Formula Ib can be prepared as illustrated by the exemplary reaction in Scheme 1.

Scheme 1: Synthetic scheme to compounds of the Formula Ib

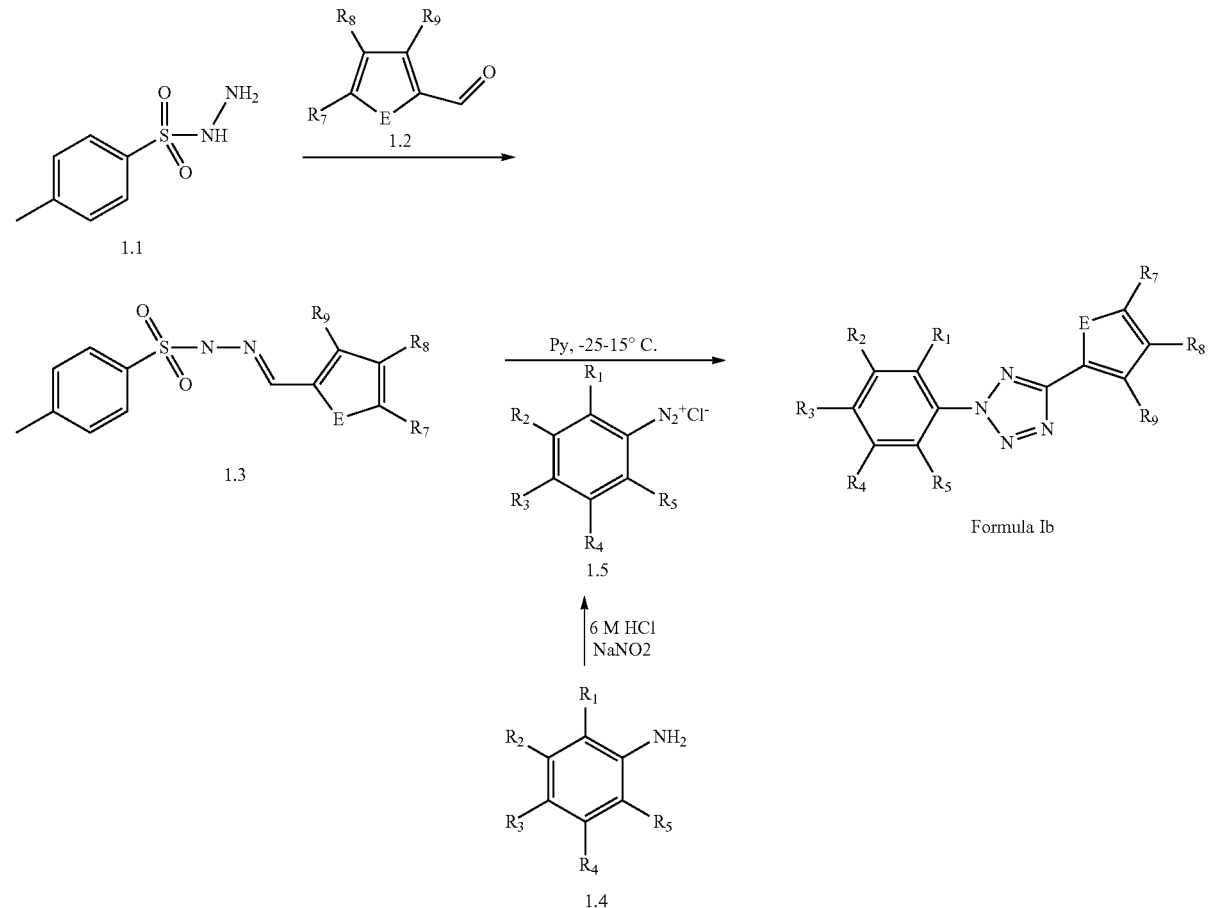

The p-methylbenzenesulfonyl hydrazine 11 is reacted with an appropriate aldehyde 1.2 in ethanol to form a corresponding p-methylbenzenesulfonyl hydrazone 1.3. Then, a solution of diazinium salt 1.5 prepared from an appropriate aryl amine 4 is added to the hydrazone 3 in pyridine at 10-15° C. to form a desired 2,5-disubstituted tetrazole of the Formula Ia.

Specifically, the compounds of this invention with Formulae Ic can be prepared as illustrated by the exemplary reaction in Scheme 2. The p-methylbenzenesulfonyl hydrazine 2.1 is reacted with an appropriate aldehyde 2.2 in ethanol to form corresponding p-methylbenzenesulfonyl hydrazone 2.3. Then, the diazinium salt 2.5 solution prepared from appropriate aryl amine 2.4 is added to hydrazone 2.3 in pyridine at 10-15° C. to form a desired 2,5-disubstituted tetrazole of the Formula Ic.

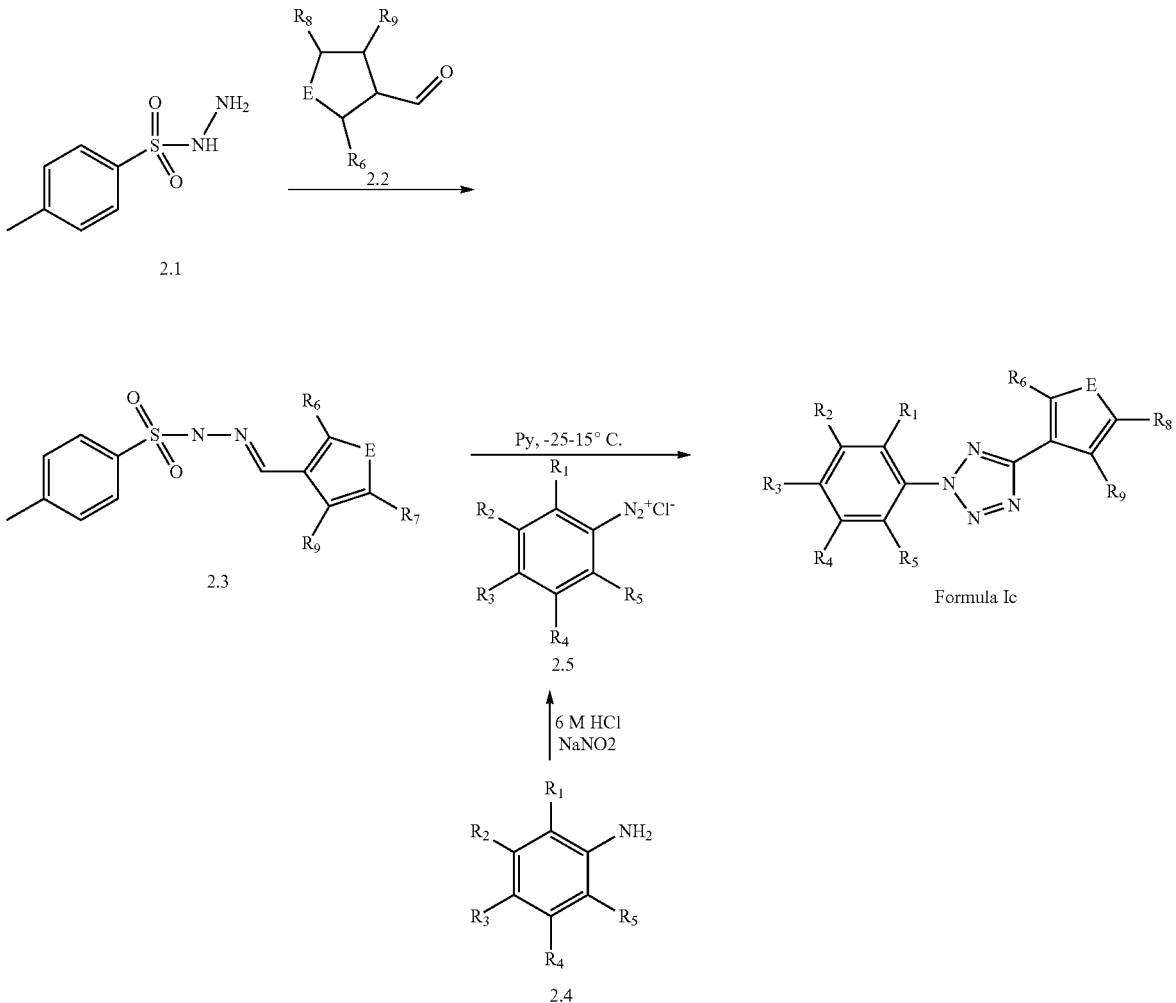

Specifically, the compounds of this invention with Formulae IIb can be prepared as illustrated by the exemplary reaction in Scheme 3. The p-methylbenzenesulfonyl hydrazine 3.1 is reacted with an appropriate aryl aldehyde 3.2 in ethanol to form corresponding p-methylbenzenesulfonyl hydrazone 3.3. Then, a solution of diazinium salt 3.5 prepared from appropriate heteroaryl amine 3.4 is added to hydrazone 2.3 in pyridine at 10-15° C. to form a desired 2,5-disubstituted tetrazole of the Formula IIb.

Scheme 3: Synthetic scheme to compounds of the Formula IIb

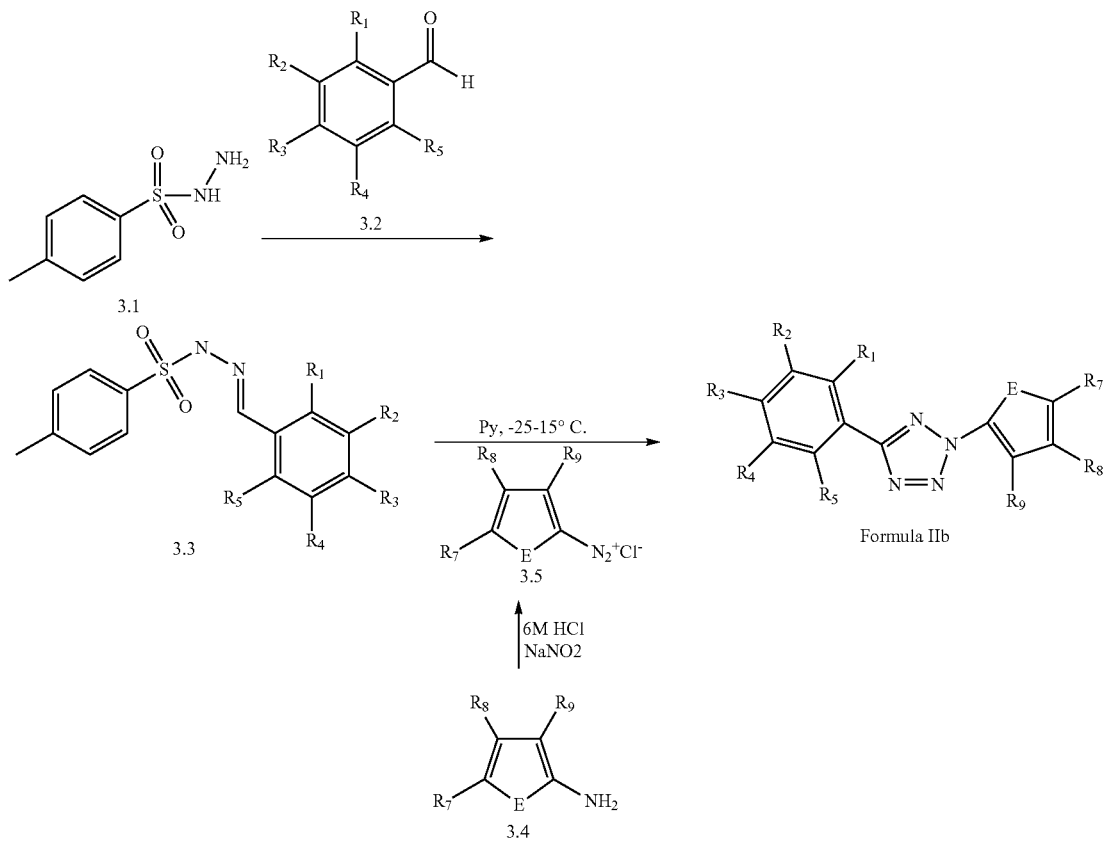

where: E = S

Specifically, the compounds of this invention with Formulae Id can be prepared as illustrated by the exemplary reaction in Scheme 4. The appropriate nitrile 4.1 was heated with sodium azide in the presence of ammonium chloride under microwave condition to form the corresponding 5-substituted tetrazole 4.2. An N-arylation of tetrazole 4.2 led to formation of two isomers that could be separated by normal phase chromatography and the desired 2,5-disubstituted tetrazole of the Formula Id could be isolated.

Scheme 4: Synthetic scheme to compounds of the Formula Id

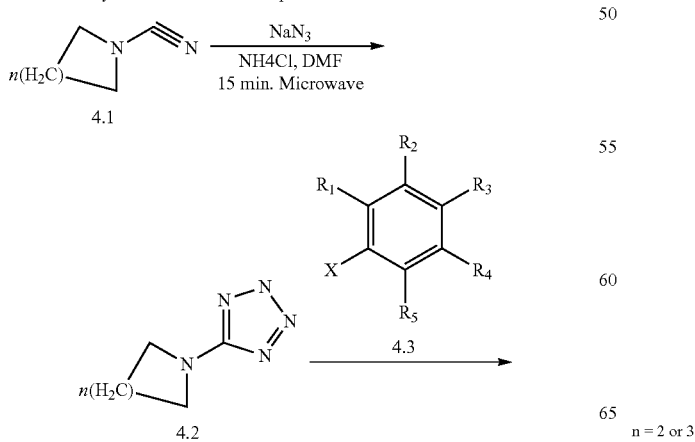

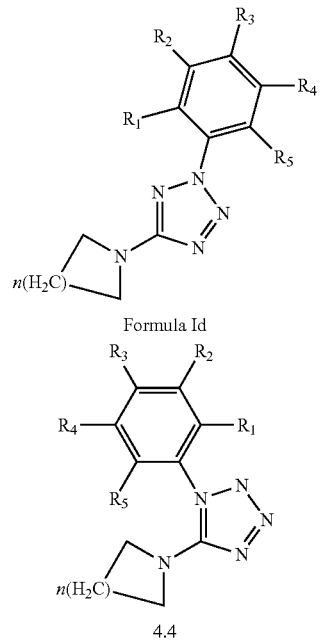

n = 2 or 3

What is claimed is:

1. A method for control of unwanted nematodes, the method comprising administering to a plant, a seed, or soil a composition comprising an effective amount of a compound of Formula I or Formula II, or a salt thereof,

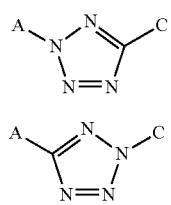

Formula I

Formula II wherein,
A is selected from the group consisting of aryl, arylalkyl, aryloxo, arylthio, heteroaryl, heteroarylalkyl, heteroaryloxo, and heteroarylthio, each of which may be optionally substituted with one or more substituents selected from the group consisting of halo, $C_1$-$C_6$ haloalkyl, $C_6$-$C_{10}$ aryl, $C_4$-$C_7$ cycloalkyl, $C_1$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$)alkenyl, $C_6$-$C_{10}$ aryl($C_2$-$C_6$) alkynyl, $C_1$-$C_6$ hydroxyalkyl, amino, ureido, cyano, $C_1$-$C_6$ acylamino, hydroxy, thiol, $C_1$-$C_6$ acyloxy, azido, $C_1$-$C_6$ alkoxy and carboxy, and C(H)O;
and
C is a heteroaryl selected from the group consisting of thienyl, furanyl, oxazolyl, or isoxazolyl, each of which can be optionally independently substituted with one or more substituents selected from the group consisting of F, Cl, Br, $CF_3$, $CH_3$ and $OCF_3$, or C is selected from the group consisting of pyrrolidinyl, piperidinyl, pyrrolyl, pyrrolyloxo, pyrrolythio, and pyrrolylalkyl, each of which can be optionally independently substituted with one or more substituents selected from the group consisting of methyl, alkyl, cycloalkyl, heterocycle, hydroxyalkyl and halogen.

2. The method of claim 1 wherein the compound is of Formula Ia or a salt thereof,

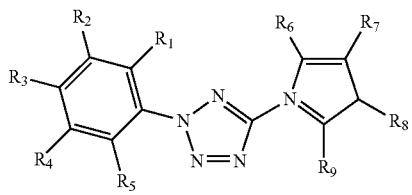

Formula Ia wherein,
$R_1$ and $R_5$ are independently selected from the group consisting of hydrogen, $CH_3$, F, Cl, Br, $CF_3$ and $OCF_3$;
$R_2$ and $R_4$ are independently selected from the group consisting of hydrogen, F, Cl, Br, and $CF_3$;
$R_3$ is selected from the group consisting of hydrogen, $CH_3$, $CF_3$, F, Cl, Br, $OCF_3$, $OCH_3$, CN, and C(H)O; and
$R_6$, $R_7$, $R_8$ and $R_9$ are independently selected from the group consisting of hydrogen, $CH_3$, $C_2$-$C_4$ alkyl, cycloalkyl, heterocyle, and halogen.

3. The method of claim 1 wherein the compound is of Formula Ib or a salt thereof,

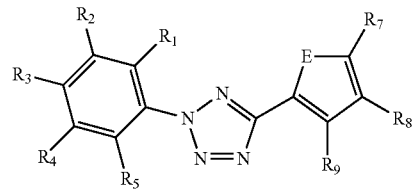

Formula Ib wherein,
$R_1$ and $R_5$ are independently selected from the group consisting of hydrogen, $CH_3$, F, Cl, Br, $CF_3$, and $OCF_3$;
$R_2$ and $R_4$ are independently selected from the group consisting of hydrogen, F, Cl, Br, and $CF_3$:
$R_3$ is selected from the group consisting of hydrogen, $CH_3$, $CF_3$, F, Cl, Br, $OCF_3$, $OCH_3$, CN, and C(H)O;
$R_7$, $R_8$ and $R_9$ are independently selected from the group consisting of hydrogen, F, Cl, Br, $CH_3$, and $OCF_3$; and
E is O or S.

4. The method of claim 3 wherein E is O.

5. The method of claim 3 wherein E is S.

6. The method of claim 1 wherein the compound is of Formula Ic or a salt thereof,

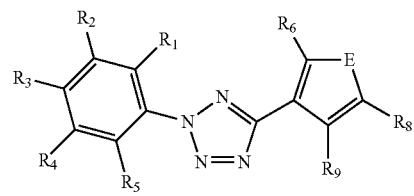

Formula Ic wherein,
$R_1$ and $R_5$ are independently selected from the group consisting of hydrogen, $CH_3$, F, Cl, Br, $CF_3$, and $OCF_3$;
$R_2$ and $R_4$ are independently selected from the group consisting of hydrogen, F, Cl, Br, and $CF_3$;
$R_3$ is selected from the group consisting of hydrogen, $CH_3$, $CF_3$, F, Cl, Br, $OCF_3$, $OCH_3$, CN, and C(H)O;
$R_6$, $R_8$ and $R_9$ are independently selected from the group consisting of hydrogen, F, Cl, Br, $CH_3$, and $OCF_3$; and
E is O or S.

7. The method of claim 6 wherein E is O.

8. The method of claim 6 wherein E is S.

9. The method of claim 1 wherein the compound is of Formula Id or a salt thereof,

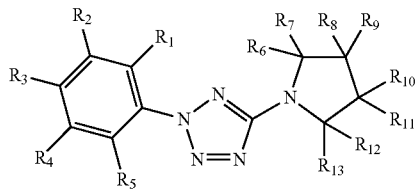

Formula Id wherein,
$R_1$ and $R_5$ are independently selected from the group consisting of hydrogen, $CH_3$, F, Cl, Br, $CF_3$ and $OCF_3$;

$R_2$ and $R_4$ are independently selected from the group consisting of hydrogen, F, Cl, Br, and $CF_3$;

$R_3$ is selected from the group consisting of hydrogen, $CH_3$, $CF_3$, F, Cl, Br, $OCF_3$, $OCH_3$, CN, and C(H)O;

$R_6$ through $R_{13}$ are independently selected from the group consisting of hydrogen, $CH_3$, $C_2$-$C_4$ alkyl, cycloalkyl, heterocyle, and halogen.

10. The method of claim 1 wherein the compound is of Formula IIa or a salt thereof,

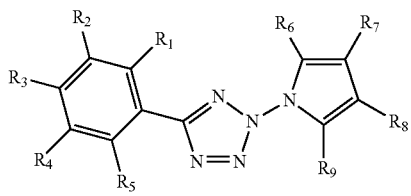

Formula IIa wherein, $R_1$ and $R_5$ are independently selected from the group consisting of hydrogen, $CH_3$, F, Cl, Br, $CF_3$ and $OCF_3$;

$R_2$ and $R_4$ are independently selected from the group consisting of hydrogen, F, Cl, Br, and $CF_3$;

$R_3$ is selected from the group consisting of hydrogen, $CH_3$, $CF_3$, F, Cl, Br, $OCF_3$, $OCH_3$, CN, and C(H)O; and $R_6$, $R_7$, $R_8$ and $R_9$ are independently selected from the group consisting of hydrogen, $CH_3$, alkyl, cycloalkyl, heterocyle, and halogen.

11. The method of claim 1 wherein the compound is of Formula IIb or a salt thereof,

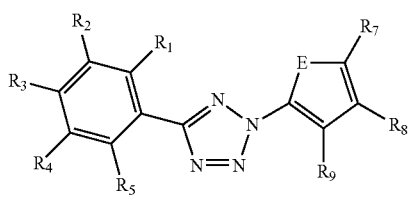

Formula IIb wherein, $R_1$ and $R_5$ are independently selected from the group consisting of hydrogen, $CH_3$, F, Cl, Br, $CF_3$, and $OCF_3$;

$R_2$ and $R_4$ are independently selected from the group consisting of hydrogen, F, Cl, Br, and $CF_3$;

$R_3$ is selected from the group consisting of hydrogen, $CH_3$, $CF_3$, F, Cl, Br, $OCF_3$, $OCH_3$, CN, and C(H)O;

$R_7$, $R_8$ and $R_9$ are independently selected from the group consisting of hydrogen, F, Cl, Br, $CH_3$, and $OCF_3$; and E is O or S.

12. The method of claim 11 wherein E is O.

13. The method of claim 11 wherein E is S.

14. The method of claim 1 wherein the compound is of Formula IIc or a salt thereof,

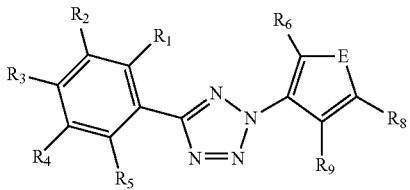

Formula IIc wherein, $R_1$ and $R_5$ are independently selected from the group consisting of hydrogen, $CH_3$, F, Cl, Br, $CF_3$, and $OCF_3$;

$R_2$ and $R_4$ are independently selected from the group consisting of hydrogen, F, Cl, Br, and $CF_3$;

$R_3$ is selected from the group consisting of hydrogen, $CH_3$, $CF_3$, F, Cl, Br, $OCF_3$, $OCH_3$, CN, and C(H)O;

$R_6$, $R_8$ and $R_9$ are independently selected from the group consisting of hydrogen, F, Cl, Br, $CH_3$, and $OCF_3$; and E is O or S.

15. The method of claim 14 wherein E is O.

16. The method of claim 14 wherein E is S.

17. The method of claim 1 wherein the compound is of Formula IId or a salt thereof,

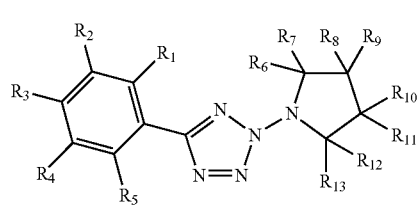

Formula IId wherein, $R_1$ and $R_5$ are independently selected from the group consisting of hydrogen, $CH_3$, F, Cl, Br, $CF_3$ and $OCF_3$;

$R_2$ and $R_4$ are independently selected from the group consisting of hydrogen, F, Cl, Br, and $CF_3$;

$R_3$ is selected from the group consisting of hydrogen, $CH_3$, $CF_3$, F, Cl, Br, $OCF_3$, $OCH_3$, CN, and C(H)O; and $R_6$ through $R_{13}$ are independently selected from the group consisting of hydrogen, $CH_3$, alkyl, cycloalkyl, heterocyle, and halogen.

18. The method of claim 1 wherein the compound is selected from the group consisting of:
2-phenyl-5-(thiophen-2-yl)-2H-tetrazole,
5-(furan-2-yl)-2-phenyl-2H-tetrazole,
2-(4-chlorophenyl)-5-(thiophen-2-yl)-2H-tetrazole,
2-(4-chlorophenyl)-5-(furan-2-yl)-2H-tetrazole,
2-(4-chloro-2-methylphenyl)-5-(thiophen-2-yl)-2H-tetrazole,
2-(4-chloro-2-methylphenyl)-5-(furan-2-yl)-2H-tetrazole,
5-phenyl-2-(thiophen-2-yl)-2H-tetrazole, 2-(furan-2-yl)-5-phenyl-2H-tetrazole,
5-(4-chlorophenyl)-2-(thiophen-2-yl)-2H-tetrazole,
5-(4-chlorophenyl)-2-(furan-2-yl)-2H-tetrazole,
5-(4-chloro-2-methylphenyl)-2-(thiophen-2-yl)-2H-tetrazole,
5-(4-chloro-2-methylphenyl)-2-(furan-2-yl)-2H-tetrazole,
and salts thereof.

19. The method of claim 1 wherein the composition comprises one or more of a fungicide, an herbicide, or another pesticide.

20. The method of claim 1 wherein the composition is applied to a seed.

21. A treated seed prepared by the method of claim 20.

* * * * *

UNITED STATES PATENT AND TRADEMARK OFFICE
CERTIFICATE OF CORRECTION

PATENT NO. : 9,339,035 B2
APPLICATION NO. : 13/819880
DATED : May 17, 2016
INVENTOR(S) : Urszula Slomczynska et al.

It is certified that error appears in the above-identified patent and that said Letters Patent is hereby corrected as shown below:

In the Claims:

Column 33, Claim 2, Lines 46-55

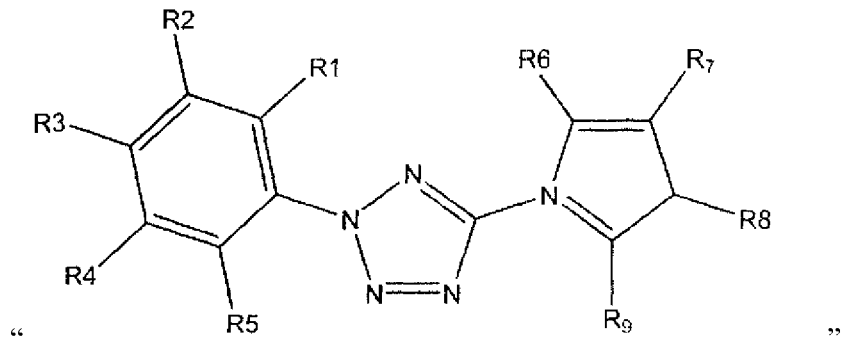

"                                                                "

Should read

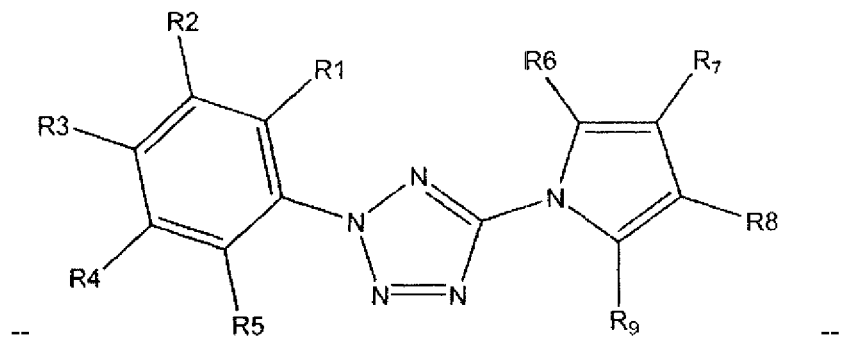

--                                                                --

Signed and Sealed this
Ninth Day of August, 2016

Michelle K. Lee
*Director of the United States Patent and Trademark Office*